United States Patent [19]

Lednicer

[11] 3,953,425

[45] Apr. 27, 1976

[54] AZEPINE INDANYL AND TETRALIN BUTYROPHENONES

[75] Inventor: Daniel Lednicer, Portage, Mich.

[73] Assignee: The Upjohn Company, Kalamazoo, Mich.

[22] Filed: Sept. 6, 1974

[21] Appl. No.: 503,645

[52] U.S. Cl. .................. 260/239 B; 260/239.3 T; 260/293.62; 260/326.81; 260/340.5; 260/340.9; 260/473 F; 260/566 A; 260/61 BF; 260/590 R; 424/244; 424/274; 424/256; 260/566 AE; 260/590 FA

[51] Int. Cl.$^2$ ............... C07D 223/32; C07D 223/14

[58] Field of Search ....... 260/239 B, 293.62, 326.81

[56] References Cited
FOREIGN PATENTS OR APPLICATIONS
929,739   6/1963   United Kingdom

OTHER PUBLICATIONS

Tokura et al., Bull. Chem. Soc. Japan, 37, 138 (1964).

Roberts et al., Basic Princ. of Org. Chem. 1964, pp. 659, 661.

Nice et al., J. Med. Chem. 9, 765 (1966).

Rice et al., J. Med. Chem. Vol. 6, 388 (1963).

Grogan et al., J. Med. Chem. Vol. 8, 62, (1965).

*Primary Examiner*—Raymond V. Rush
*Assistant Examiner*—Mark L. Berch
*Attorney, Agent, or Firm*—John T. Reynolds; Ward F. Nixon

[57]                ABSTRACT

Novel azepine spiro indans, azepine spiro tetralins, pharmacologically acceptable acid addition salts thereof and processes for their production. The compounds of this invention and the pharmacologically acceptable acid addition salts thereof have central nervous system activity, they are especially useful as central nervous system depressants.

2 Claims, No Drawings

AZEPINE INDANYL AND TETRALIN BUTYROPHENONES

SUMMARY OF THE INVENTION

The novel compounds of this invention are illustratively represented by the following generic formula 1:

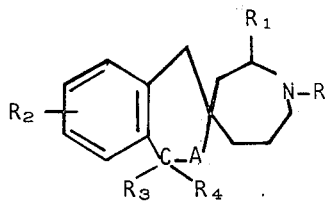

wherein R is

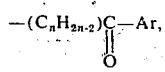

in which n is a whole number from 2 to 5, inclusive, and Ar is phenyl having 0 to 3 substituents selected from the group consisting of alkyl of 1 to 3 carbon atoms, inclusive, alkoxy of 1 to 3 carbon atoms, inclusive, bromine, chlorine and fluorine, or R is

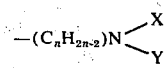

in which n has the meaning given above, X and Y taken separately are alkyl of 1 to 3 carbon atoms, inclusive, or X and Y taken together with

is a saturated heterocyclic amino radical selected from the group consisting of unsubstituted and substituted pyrrolidino, piperidino and hexamethylenimino; $R_1$ is hydrogen, or alkyl of 1 to 3 carbon atoms, inclusive; $R_2$ is hydrogen, alkyl of 1 to 3 carbon atoms, inclusive, alkoxy of 1 to 3 carbon atoms, inclusive, chlorine, fluorine, bromine, or trifluoromethyl taken separately $R_3$ is hydrogen, and $R_4$ is hydrogen, or hydroxy and taken together $R_3$ and $R_4$ are methylene; A is a valence bond or methylene, and the pharmacologically acceptable acid addition salts of the compounds of formula 1.

The more desirable compounds of this invention are represented by the following formula:

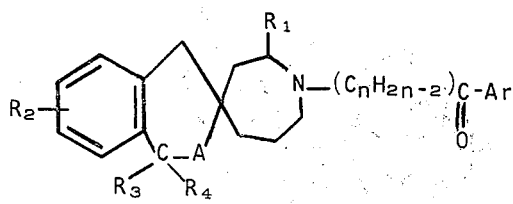

IA wherein $n$, Ar, $R_1$, $R_2$, $R_3$, $R_4$ and A have the meanings previously given, and the pharmacologically acceptable acid addition salts thereof.

The most preferred compounds of the invention are represented by the following formulas:

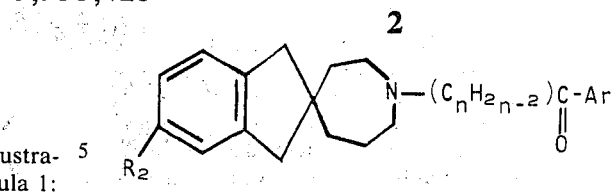

IB

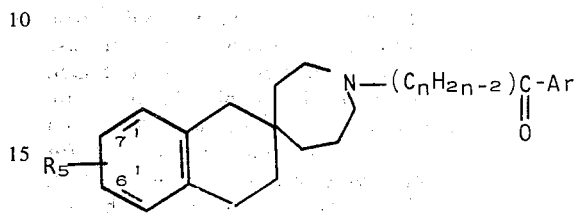

IC wherein $n$, Ar, and $R_2$ have the meanings previously given; and $R_5$ is hydrogen, alkyl of 1 to 3 carbon atoms, inclusive, alkoxy of 1 to 3 carbon atoms, inclusive, chlorine or bromine, and is attached at either the 6' or 7' position of the aromatic ring and the pharmacologically acceptable acid addition salts thereof.

Examples of Ar are phenyl, m-chlorophenyl, p-fluorophenyl, m-ethylphenyl, o-methylphenyl, 3,4-dimethoxyphenyl, 2,4-dimethylphenyl, 2-bromo-5-ethylphenyl, 2-chloro-3,5-dipropylphenyl and 2,4,6-trichlorophenyl, Examples of lower alkyl of 1 through 3 carbon atoms are methyl, ethyl, propyl and isopropyl. Examples of lower alkoxy of 1 through 3 carbon atoms are methoxy, ethoxy, propoxy, and isopropoxy. Examples of unsubstituted and substituted pyrrolidino, piperidino and hexamethylenimino are pyrrolidino, 2-methylpyrrolidino, piperidino, 2-ethylpiperidino, hexamethylenimino, 3-methoxyhexamethylenimino and 2-ethyl-4-methylhexamethylenimino. Examples of

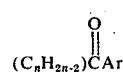

is phenyl having from zero through three substituents selected from the group consisting of fluorine, chlorine, bromine, lower alkyl of 1 through 3 carbon atoms and lower alkoxy of 1 through 3 carbon atoms, are: 4-oxo-4-(p-fluorophenyl)butyl, 4-oxo-4-(2-chloro-1-methylphenyl)butyl, 4-oxo-4-phenylbutyl, 4-oxo-4-(p-tolyl)-butyl, 4-oxo-4-(p-methoxyphenyl)butyl, 4-oxo-4-(p-chlorophenyl)butyl, 4-oxo-(2-bromo-4-chlorophenyl)-butyl, 3-oxo-3-(p-bromophenyl)propyl, 5-oxo-4-(o-ethoxyphenyl)pentyl, and the isomeric forms thereof. Examples of

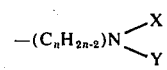

in which X and Y are taken separately are 4-dimethylaminobutyl, 4-methyl-4-ethylaminobutyl, 4-methyl-4-isopropylaminobutyl, 2-diethylaminopropyl, 2-methyl-2-propylaminoethyl, 5-dimethylaminopentyl, and the like, examples in which X and Y are taken together are, 4-pyrrolidinobutyl, 3-piperidinopropyl, 2-(2-ethylpiperidino)ethyl, 5-hexamethyleniminopentyl, 4-(3-methoxyhexamethylenimino)butyl and the like.

The novel compounds of formula I, IA, IB and IC exist either in the non-protonated (free base) form or in the protonated (acid addition salt) form, depending on the pH of the environment. They form stable protonates, i.e., acid addition salts, on neutralization of the free base form with suitable acids, for example, hydrochloric, hydrobromic, sulfuric, phosphoric, nitric, acetic, propionic, palmitic, benzoic, salicylic, hexynoic, phenylbutyric, naphthoic, glycolic, succinic, nicotinic, tartaric, maleic, malic, pamoic, methanesulfonic, citric and lactic acids, and the like. Conversely, the free base of the novel compounds of Formula I can be obtained from a salt (e.g., from the hydrochloride or sulfate salts) by neutralization with a base such as sodium hydroxide, extracting with an immiscible solvent, for example chloroform, drying the extract, for example, with anhydrous sodium sulfate, and removing the solvent by evaporation.

The free bases and acid addition salts of the novel compounds of Formula I, IA, IB and IC are useful as central nervous system (CNS) depressants when administered to humans and animals. They possess tranquilizing activity and are consequently useful in humans for controlling anxiety and schizophrenia; in animals the aforesaid compounds are useful for their calming effects and can be given to reduce aggressive behavior.

As tranquilizers, the compounds of Formulas I, IA, IB and IC and their pharmacologically acceptable acid addition salts are prepared and administered to humans, mammals, birds and animals in a wide variety of oral, rectal, and parenteral dosage forms, singly or in admixture with other coacting compounds, in doses of from about 1 mg. to about 20 mg./kg., depending on the severity of the condition being treated and the recipient's response to the medication. For example, 100 mg. of the compound of Example 6 hereinafter is initially administered orally to a 70 kg. human four times per day, the amount or frequency of the dose then being increased or decreased in accord with the initial response of the human.

The compounds of formula I, IA, IB and IC are preferably administered with a pharmaceutical carrier which can be solid material or a liquid in which the compound is dissolved, dispersed or suspended. The solid compositions takes the form of tablets, powders, suppositories, capsules, pills or the like, preferably in unit dosage forms for simple administration or precise dosages. The liquid compositions can take the form of solutions, emulsions, suspensions, syrups, or elixirs.

DETAILED DESCRIPTION OF THE INVENTION

The novel compounds of Formula I (including IA, IB and IC) of this invention are prepared in accordance with the following reaction sequence:

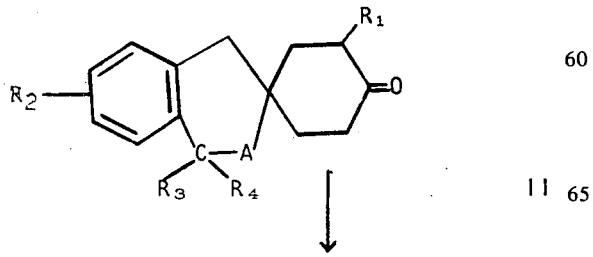

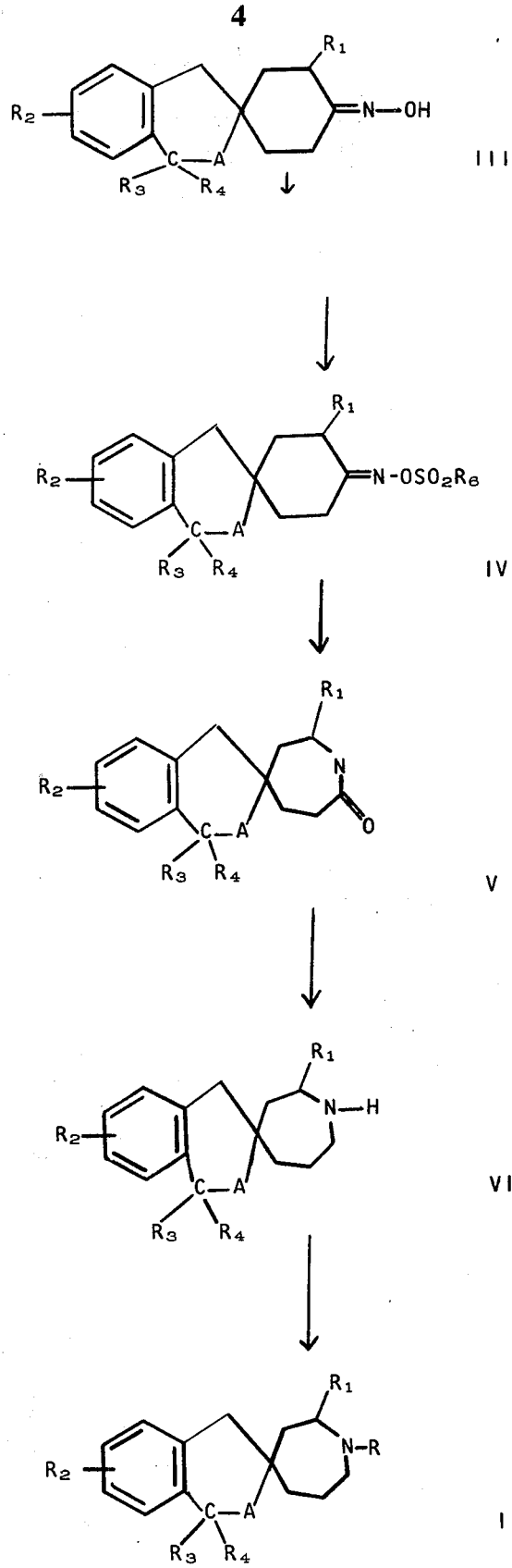

wherein R, $R_1$, $R_2$, $R_3$, $R_4$ and A have the meanings previously given and $R_6$ is phenyl, p-tolyl or alkyl of 1 to 3 carbon atoms, inclusive.

The starting materials of formula II are prepared in accordance with methods hereinafter described.

The compounds embraced by formula I, which is inclusive of the compounds of formulas IA, IB and IC, are prepared by employing the methods and reactions described below.

1. The first step of the process comprises reacting a spiro (cyclohexane-1,2'-indan)-4-one (II) or a 3',4'-dihydrospiro[cyclohexane-1,2'(1'H)-naphthalen]-4-one (II) with an acid addition salt of hydroxylamine and an alkali metal hydroxide such as sodium hydroxide at reflux temperature for from about 4 to about 8 hours to obtain the corresponding spiro(cyclohexane-1,2'-indan)-4-one oxime (III) or the corresponding 3',4'-dihydrospiro[cyclohexane-1,2'-(1'H)naphthalen]-4-one oxime (III), respectively.

2. The selected oxime from step I., above, in an amine base (e.g., pyridine) is treated with an aryl or alkyl sulfonyl halide, such as a lower alkyl sulfonyl halide (e.g., methanesulfonyl chloride) or p-toluene sulfonyl chloride or benzene sulfonyl chloride, p-toluene sulfonyl chloride is preferred, and allowed to let stand at low temperature (e.g., an ice bath) for from about 3 to about 18 hours to obtain the corresponding sulfonate (IV).

3. The selected sulfonate (IV) obtained in step 2., above, is then treated with a lower alkanoic acid preferably of from 1 to 4 carbon atoms, inclusive, such as formic acid, acetic acid, propionic acid, butyric acid and the like, acetic is especially advantageous, and refluxed for from about 3 to 10 hours to obtain the corresponding lactam (V).

4. The lactam (V) thus obtained, is then dissolved in an inert organic solvent such as tetrahydrofuran and reacted with a reducing agent such as lithium aluminum hydride or diborane at temperatures from room temperature to reflux conditions for a period of from about 2 to about 8 hours to obtain the corresponding compound of Formula (VI), which on dissolving in ether and treating with an ethereal solution of an appropriate acid gives a corresponding acid addition salt thereof.

5. The compounds obtained in step 4 above; the selected 1,2,3,5,6,7-hexahydro spiro[4H-azepine-4,2'-indane] or 1,2,3,3',4',5,6,7-octahydrospiro[4H-azepine-4,2'(1'H)naphthalene] (the free base) is then dissolved in an appropriate solvent such as dimethylformamide, benzene, toluene, and the like and reacted with a ketal of a haloalkyl aryl ketone of the formula:

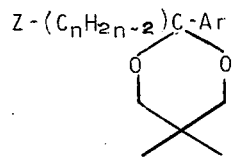

wherein Ar and n have the meanings previously given and Z is halogen and

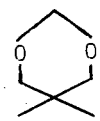

represents a ketal group such as an alkylene ketal e.g., ethylene ketal, propylene ketal; neopentyl glycol ketal and the like; or a haloalkyl amine of the formula:

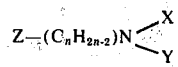

wherein X, Y, Z and n have the meanings previously given; representative compounds of the above formulas which can be used are for example 4-chloro-4'-fluorobutyrophenone neopentyl glycol ketal, 5-bromo-4'-chlorovalerophenone propylene ketal, 3-chloro-propiophenone ethylene ketal, 4-bromo-4'-methyl-butyrophenone neopentyl glycol ketal 6-bromo-4'-fluorocapriophenone propylene ketal, 3-chloro-N,N-dimethylpropylamine, 4-bromo-N,N-diethylbutylamine, 3-chloro-N-methyl-N-ethylpropylamine, 5-chloro-N-methyl-N-propylpentylamine, to obtain the products of formula I. The reaction is carried out at a temperature within the range of from about 50° to about 120° C. for a period of from about 3 to about 20 hours. A temperature within the range of from 80° to 100 °C. is preferred. The compounds of formula I are converted to their acid addition salts in the manner disclosed in step 4 above.

All of the compounds included within Formula I and the intermediates III through VI of the flow-sheet, above, can be isolated from their respective reaction mixtures by conventional means, for example, when a water-miscible solvent is used, by pouring the reaction mixture into water and separating the resulting precipitate fy filtration or by extraction with water-immiscible solvents. Additional purification of the products can be accomplished by conventional means, for example, by elution chromatography from an adsorbent column with a suitable solvent such as acetone, ethyl acetate, ether, methylene chloride and Skellysolve B (hexanes), mixtures and combinations of these solvents; also by gradient elution chromatography from an adsorbent column with a suitable mixture of solvents, such as, methylene chloride-Skellysolve B, acetone-Skellysolve B, and the like.

Process A

The starting materials of formula II wherein A is a valence bond and $R_1$ is hydrogen, are prepared in accordance with the following reaction sequence:

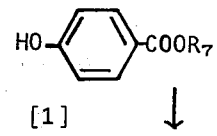

[1]

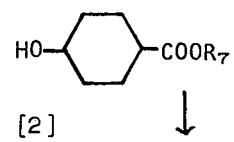

[2]

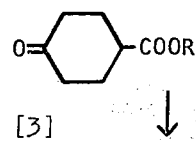

[3]

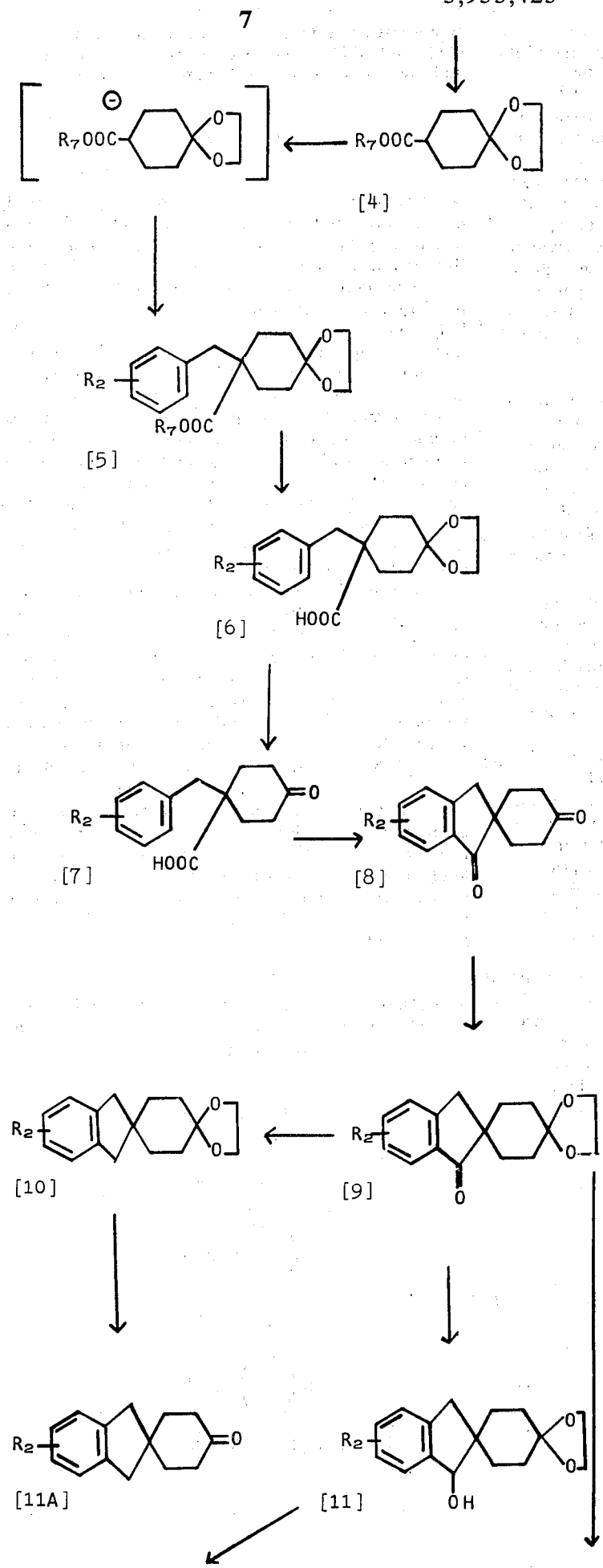

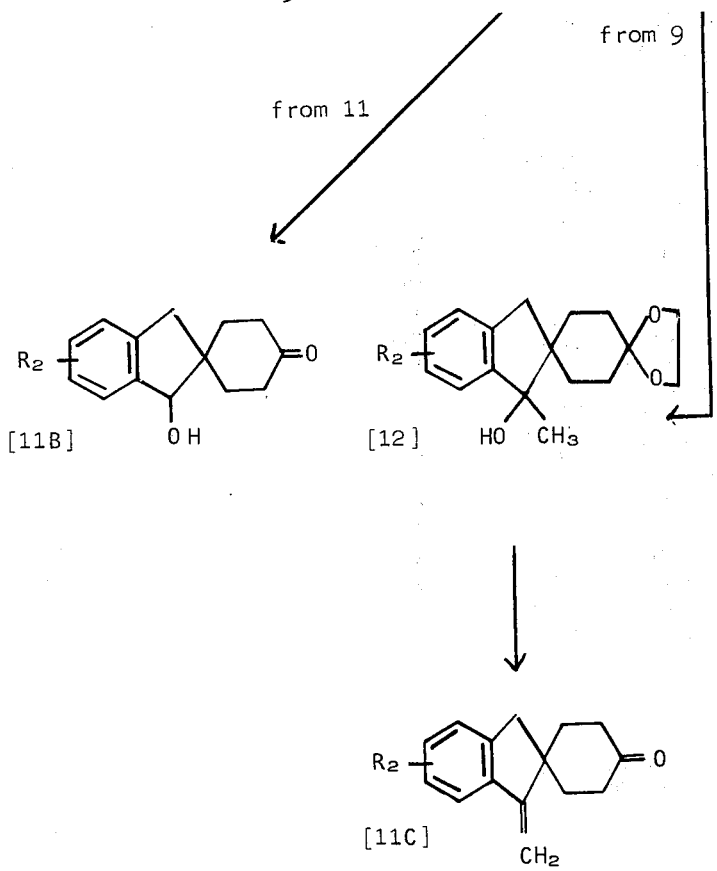

wherein $R_2$ has the meanings previously given, and $R_7$ is selected from the group consisting of alkyl of from 1 to 3 carbon atoms inclusive.

1. The first step of the process comprises reducing an alkyl p-hydroxy benzoate [1] (prepared as in Ann. 141, 247), e.g., by hydrogenating it in the presence of a catalyst (such as 5 percent rhodium/aluminum) in a solvent (such as absolute ethanol) at room temperature, to yield a corresponding alkyl-4-hydroxycyclohexane carboxylate [2].

2. An alkyl-4-hydroxycyclohexane carboxylate [2] obtained in step (1) is oxidized at the 4-position, e.g., in acetone with Jones reagent at low temperature (at from about 5° to about 20° C.) to give a corresponding 4-carboalkoxy-1-cyclohexanone [3].

3. A 4-carboalkoxy-1-cyclohexanone [3] prepared in step (2) is ketalized at the 4-position, e.g., by heating (at reflux) in benzene with an alkylene glycol (in the presence of a catalyst such as p-toluenesulfonic acid) for from about 4 to about 8 hours, to yield a corresponding 4-carboalkoxy-1-cyclohexanone alkylene ketal [4].

4. A 4-carboalkoxy-1-cyclohexanone alkylene ketal [4] obtained in step (3) on reaction with lithium diisopropyl amide (prepared by adding butyl lithium in a solvent such as pentane to diisopropylamine in a solvent such as tetrahydrofuran at low temperature) followed by addition of a benzyl halide (such as α-bromotoluene, α-chloro-p-xylene, α-bromo-m-xylene, m-methoxybenzyl chloride, and the like), yields a corresponding 4-benzyl (or substituted benzyl)-4-carboalkoxy-1-cyclohexane ketal [5].

5. A 4-benzyl (or substituted benzyl)-4-carboalkoxy-1-cyclohexane alkylene ketal [5] obtained in step (4) is saponified, e.g., by heating (at reflux for from about 10 to about 24 hours) in a solvent such as ethylene glycol with an alkali metal hydroxide (such as potassium hydroxide), to give a corresponding 4-benzyl (or substituted benzyl)-4-carboxy-1-cyclohexanone alkylene ketal [6].

6. A 4-benzyl (or substituted benzyl)-4-carboxy-1-cyclohexanone alkylene ketal [6] prepared in step (5) is deketalized, e.g., by stirring it with a dilute aqueous acid (e.g., hydrochloric acid) in acetone at moderate (room) temperature for from about 6 to about 60 hours, to give a corresponding 1-benzyl (or substituted benzyl)-4-cyclohexanone-1-carboxylic acid [7].

7. Reacting a 1-benzyl (or substituted benzyl)-4-cyclohexanone-1-carboxylic acid [7] obtained in step (6) with hydrogen fluoride at room temperature (or with phosphorus pentachloride at reflux temperature, followed by treatment with stannic chloride), gives a corresponding unsubstituted or substituted spiro(cyclohexane-1,2'-indan)-1'4-dione [8].

8. An unsubstituted or substituted spiro(cyclohexane-1,2'-indan)-1'4-dione [8] obtained in step (7) is ketalized at the 4-position, e.g., by heating (at reflux) in benzene with an alkylene glycol (in the presence of a catalyst such as p-toluenesulfonic acid) for from about 3 to 7 hours, to yield a corresponding unsubstituted or substitued spiro(cyclohexane-1,2'-indan)-1',4-dione 4-alkylene ketal [9].

9. A spiro(cyclohexane-1,2'-indan)-1'4-dione 4-alkylene ketal [9] prepared in step (8) on being subjected to Wolff-Kischner reduction, namely, by heating it (at reflux) with hydrazine hydrate and an alkali metal hydroxide (such as potassium hydroxide) in a solvent such as ethylene glycol for from about 8 to about 12 hours, gives a corresponding spiro(cyclohexane-1,2'-indan)-4-one alkylene ketal [10].

10. A spiro(cyclohexane-1,2'-indan)-4-one alkylene ketal [10] obtained in step (9) is deketalized, e.g., by stirring it with a dilute aqueous acid (such as hydrochloroic acid) in acetone for from about 3 to about 8 hours, to give a corresponding spiro(cyclohexane-1,2'-indan)-4-one, [IIA].

The unsubstituted and substituted spiro(cyclohexane-1,2'-indan)-1,4'-dione alkylene ketals [9] prepared in step (8) above can be employed as starting materials for producing a variety of 1'-substituted spiro(cyclohexane-1,2'-indan) compounds of formula II by the procedures that follow.

11. A spiro(cyclohexane-1,2'-indan)-1'4-dione alkylene ketal [9] has its 1'-keto function reduced, e.g., by reacting said compound with lithium aluminum hydride in a solvent such as tetrahydrofuran at moderate (room) temperature for from about 3 to about 10 hours, yields a corresponding 1'-hydroxyspiro(cyclohexane-1,2'-indan)-4-one alkylene ketal [11].

12. A 1'-hydroxyspiro(cyclohexane-1,2'-indan)-4-one alkylene ketal [11] produced in step (11) has its ketal protective group removed by hydrolysis, e.g., by allowing said compound to stand for from about 4 to about 20 hours with an acid (such as hydrochloric acid) in a solvent (such as acetone) at room temperature, to yield a corresponding 1'-hydroxyspiro(cyclohexane-1,2'-indan)-4-one, [IIB].

13. A spiro(cyclohexane-1,2'-indan)-1'4-dione-4-alkylene ketal (9) in a solvent such as tetrahydrofuran, on addition to a methyl magnesium halide (such as methyl magnesium bromide) in a solvent such as ether, after standing at moderate (room) temperature for from about 6 to about 24 hours, gives a corresponding 1'-hydroxy-1'-methylspiro(cyclohexane-1,2'-indan)-4-one alkylene ketal [12].

14. 1'-hydroxy-1'-methylspiro(cyclohexane-1,2'-indan)-4-one alkylene ketal [12] produced in step 13, on stirring with an acid (such as hydrochloric) in a solvent (such as acetone) at room temperature for from about 4 to about 20 hours, yields a corresponding 1'-exo-methylenespiro(cyclohexane-1,2'-indan)-4-one [IIC].

Process B

The starting materials of formula II wherein A is methylene and $R_1$ is hydrogen are prepared in accordance with the following reaction sequence:

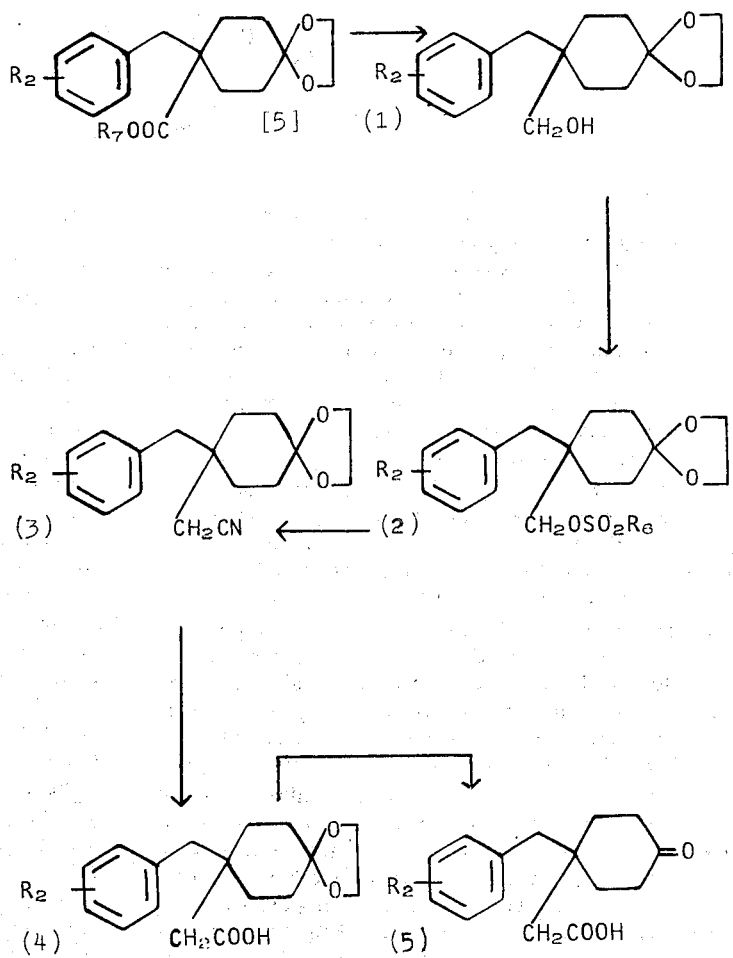

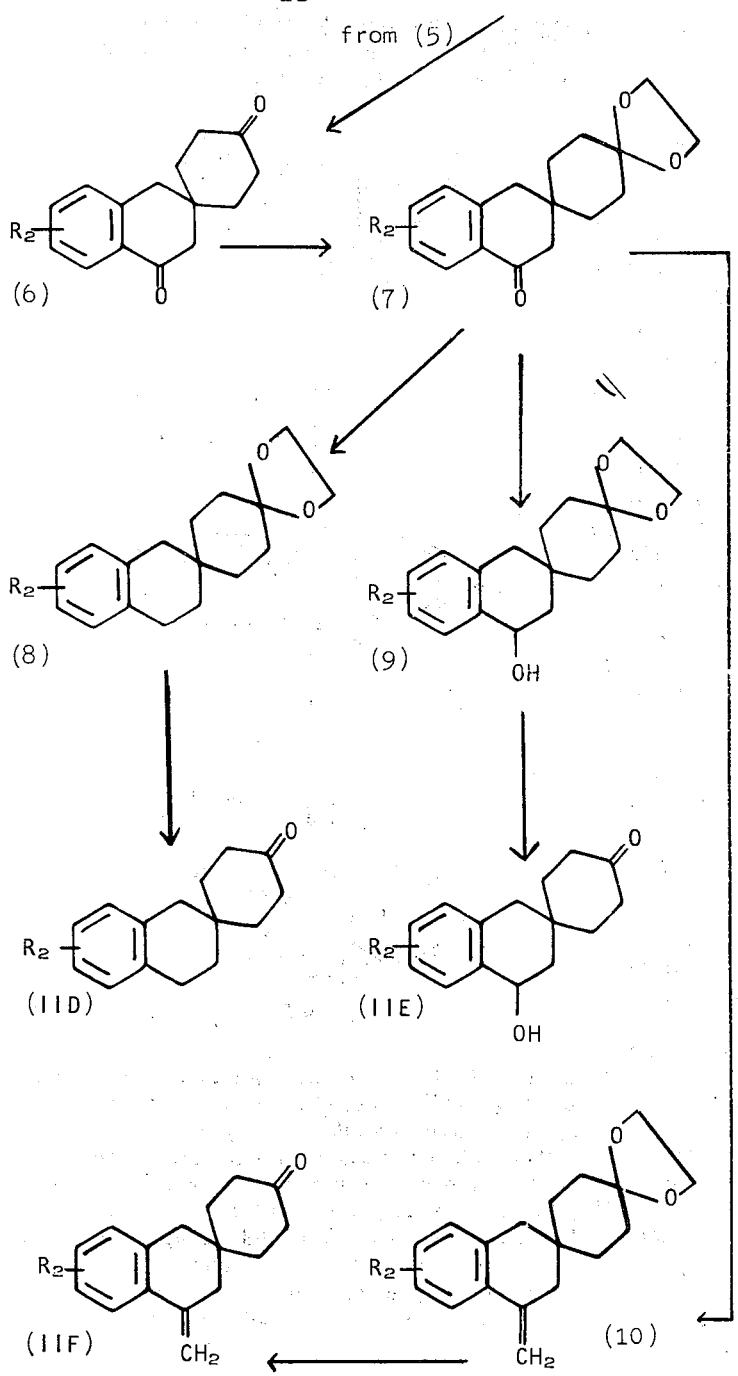

wherein $R_2$, $R_5$ and $R_6$ have the meanings previously given,

1. The first step of the process comprises reducing a 4-benzyl (or substituted benzyl)-4-carboalkoxy-1-cyclohexanone alkylene ketal [5] (prepared as above in step (4) of Process A, for example, by reacting it in a solvent such as tetrahydrofuran with lithium aluminum hydride and heating the reaction mixture (at reflux) for from about 3 to about 8 hours, to give a corresponding 4-benzyl (or substituted benzyl)-4-hydroxymethylcyclohexan-1-one alkylene ketal (1).

2. A 4-benzyl (or substituted benzyl)-4-hydroxymethylcyclohexan-1-one alkylene ketal (1) obtained in step (1) in an amine base (such as pyridine) on standing in the cold with a lower alkyl sulfonyl halide (such as methanesulfonyl chloride), yields a corresponding 4-benzyl (or substituted benzyl)-4-hydroxymethylcyclohexan-1-one, alkylene ketal, lower alkyl sulfonate (2).

3. A 4-benzyl (or substituted benzyl)-4-hydroxymethylcyclohexane-1-one, alkylene ketal lower alkyl sulfonate (2) prepared in step (2) on heating for from about 10 to about 18 hours at from about 100° to about 165° C. with potassium cyanide in a solvent such as hexamethylphosphoramide, yields a corresponding 4-benzyl-4-cyanomethylcyclohexan-1-one alkylene ketal (3).

4. A thus produced 4-benzyl-4-cyanomethylcyclohexan-1-one alkylene ketal (3) obtained in step (3) on saponification, e.g., by heating it with an alkali metal hydroxide (such as potassium hydroxide) in a solvent such as an alkalene glycol (e.g., ethylene glycol) for from about 8 to about 18 hours, gives a corresponding 4-benzylcyclohexan-4-acetic acid-1-one alkylene ketal (4).

5. A 4-benzylcyclohexan-4-acetic acid-1-one alkylene ketal (4) prepared in step (4) is deketalized, e.g., by stirring it with a dilute aqueous acid (e.g., hydrochloric) in acetone at moderate (room) temperature for from about 36 to about 72 hours, to give a corresponding 4-benzylcyclohexan-4-acetic acid-1-one (5).

6. A 4-benzylcyclohexan-4-acetic acid-1-one (5) prepared in step (5) is cyclized, e.g., by allowing it to stand at moderate (room) temperature for from about 15 to about 80 hours with liquid hydrogen fluoride, to yield a corresponding 3',4'-dihydrospiro[cyclohexane-1,2'(1'H)-naphthalene]-4',4-dione (6).

7. A 3',4'-dihydrospiro[cyclohexane-1,2'(1'H)-naphthalene]-4',4-dione (6) obtained in step (6) is monoketalized at the non-conjugated leasted hindered carbonyl function, e.g., by heating (at reflux) in a solvent such as benzene with an alkylene glycol (in the presence of a catalyst such as p-toluenesulfonic acid), to yield a corresponding 3',4'-dihydrospiro[cyclohexane-1,2'(1'H)-naphthalene]-4',4-dione, 4-(alkylene ketal) (7).

8. A 3',4'-dihydrospiro[cyclohexane-1,2'(1'H)-naphthalene]-4',4-dione, 4-(alkylene ketal) (7) prepared in step (7) is reduced at the 1'-position, e.g., by heating (at reflux) for from about ½ to about 3 hours with hydrazine hydrate and a base (e.g., potassium hydroxide) in a solvent such as an alkylene glycol (e.g., ethylene glycol), to give a corresponding 3',4'-dihydrospiro[cyclohexane-1,2'(1'H)-naphthalene]-4-one, ethylene ketal (8).

9. In this step, a 3',4'-dihydrospiro[cyclohexane-1,2'-(1'H)-naphthalen)-4-one, ethylene ketal (8) obtained in step (8) has its ketal protective group removed by hydrolysis, e.g., by heating it (at reflux) for from about 8 to about 20 hours with an acid (such as hydrochloric) in a solvent (such as acetone), to yield a corresponding 3',4'-dihydrospiro[cyclohexane-1,2'(-1'H)-naphthalen]-4-one (IID).

10. A 3',4'-dihydrospiro[cyclohexane-1,2'(1'H)-naphthalene]-4',4-dione, 4-alkylene ketal (7) has its 4' keto function reduced in accordance with the procedure disclosed in step (II) of Process A, above, to obtain the corresponding 3',4'-dihydro-4'-hydroxyspiro[cyclohexane-1,2'-(1'H)-naphthalen]-4-one, 4-alkylene ketal (9), which is deketalized as hereinbefore described to obtain the corresponding 3',4-dihydro-4'-hydroxyspiro[cyclohexane-1,2'-(1'H)-naphthalene]-4-one, (IIE).

11. A 3',4'-dihydrospiro[cyclohexane-1,2'(1'H)-naphthalene]-4',4-dione, 4-alkylene ketal (7) in a solvent such as ether on addition to methylenetriphenylphosphorane (prepared from methyltriphenylphosphonium bromide and n-butyl lithium) in a solvent such as ether, after refluxing for from about 6 to about 24 hours gives a corresponding 1'-exo-methylene-3',4'-dihydrospiro[cyclohexane-1,2'(1'H)-naphthalene]-4-one, alkylene ketal (10) which on stirring with an acid (such as hydrochloric) in a solvent (such as acetone) at room temperature for from about 4 to about 20 hours, yields a corresponding 1'-exo-methylene-3',-4'-dihydrospiro[cyclohexane-1,2'(1'H)-naphthalene]-4-one, (IIF).

The starting materials of formula II wherein $R_1$ is hydrogen, prepared in processes A and B, above, (compounds IIA, IIB, IIC, IID, IIE and IIF, represented collectively by formula IIa) are converted to the corresponding compounds of formula II wherein $R_1$ is alkyl (represented by formula IIc) below in accordance with the following reaction sequence:

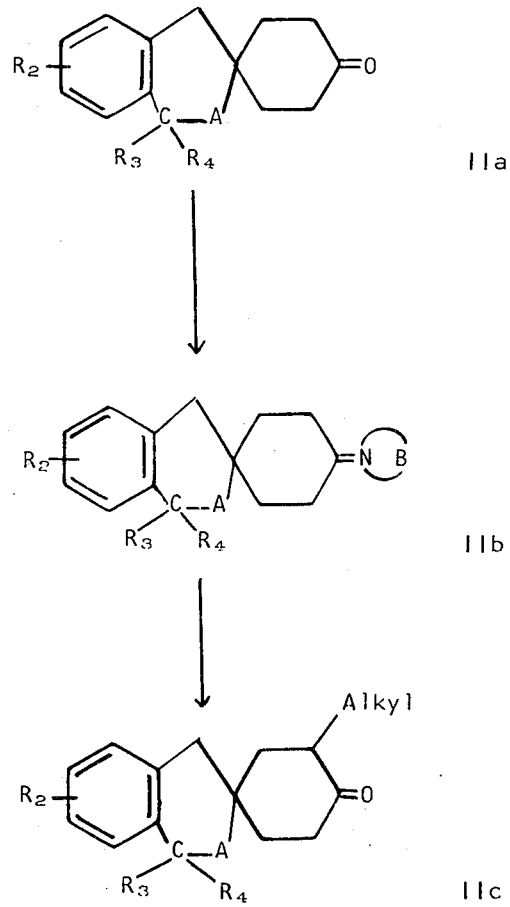

wherein $R_2$, $R_3$ and $R_4$ have the meanings previously given, "Alkyl" is an alkyl radical of 1 to 3 carbon atoms, inclusive and B is an alkylene group which together with the attached nitrogen atom forms a ring containing from 5 to 6 members, inclusive and which preferably contains less than 9 carbon atoms. The alkylated compounds of formula IIc are prepared by first converting a compound of formula IIa to the corresponding enamine of formula IIb, for example, by reaction with a secondary cyclic alkylene amine

wherein B has the meaning previously given, preferably in the presence of an acid catalyst. Examples of amines which can be used include pyrrolidine, piperidine and C-alkyl substituted pyrrolidines and piperidines, and the like. Pyrrolidine is preferred. The reaction is carried out in accordance with methods known in the art, for example, the selected compound and the amine are heated together in the presence of a suitable solvenyt such as benzene. The enamine (IIb) thus obtained is then reacted with an alkyl halide, such as methyl iodide, ethyl bromide, propyl bromide, isopropyl bromide and the like, followed by, hydrolysis in situ with an an aqueous base such as sodium hydroxide, to give the corresponding alkylated starting materials of formula IIc, which are separated from the reaction mixture by conventional methods.

The following preparations and examples are illustrative of the manner of making and using the invention and set forth the best mode contemplated by the inventor of carrying out his invention, but are not to be construed as limiting.

Preparation 1 Methyl-4-hydroxycyclohexane carboxylate [2]

A solution of 200 g. of methyl-p-hydroxybenzoate [1] (prepared as in Ann. 141, 247) in 1700 ml. of absolute ethanol has 66 g. of 5% rhodium/aluminum catalyst added thereto and then hydrogenated until no further uptake of hydrogen is observed. The catalyst is collected on a filter and the filtrate evaporated to dryness to yield 216 g. of crude methyl-4-hydroxycyclohexane carboxylate [2], as an oil.

Preparation 2 4-Carbomethoxy-1-cyclohexane [3]

The methyl-4-hydroxycyclohexane carboxylate prepared in Preparation 1 is dissolved in acetone with mechanical stirring and cooled in an ice bath to about 5° C. Jones reagent is added at a rate to keep the reaction temperature below about 20° C. for about 10 minutes. Most of the solvent is removed on a rotary evaporator and the residue taken up in 500 ml. of ether and 150 ml. of water. The organic layer is separated, washed successively with water, saturated aqueous sodium bicarbonate solution, and brine and evaporated to dryness to yield an oil, which on distillation under vacuum gives 47.4 g. of 4-carbomethoxy-1-cyclohexanone [3] having a boiling point of 82° to 85° C. at 0.55 to 0.75 mm. of Hg.

Preparation 3 4-Carbomethoxy-1-cyclohexanone ethylene ketal [4]

A mixture of 189.7 g. of 4-carbomethoxy-1-cyclohexanone [3] (obtained as in Example 2B) in 2000 ml. of benzene, 67.5 ml. of ethylene glycol and 2.7 g. of p-toluenesulfonic acid is heated at reflux under a Dean-Stark trap for about 5 hours. After cooling, the solution is washed with saturated aqueous sodium bicarbonate and brine. The oily residue remaining when the organic solvent is evaporated to dryness and is distilled under vacuum to give 231.8 g. of 4-carbomethoxy-1-cyclohexanone ethylene ketal[4] having a boiling point of 95° to 100° C. at 0.30 mm. of Hg.

Preparation 4 4-Benzyl-4-carbomethoxy-1-cyclohexanone ethylene ketal[5]

To a solution of 5 g. (0.05 M) of diisopropyl amine in 50 ml. of tetrahydrofuran cooled in ice: methanol, 32 ml. of 1.57 n-butyl lithium in pentane is added over the course of about 5 minutes. There is then added, first, 10 g. (0.05 M) of 4-carbomethoxy-1-cyclohexanone ethylene ketal[4] (obtained as in Preparation 3) in 50 ml. of tetrahydrofuran in the course of about 15 minutes, and then 8.5 g. (0.05 M) of α-bromotoluene (also named benzyl bromide) in 15 ml. of tetrahydrofuran in about 5 minutes. The clear solution is stirred at room temperature for about 1 hour, cooled in ice and treated with 50 ml. of saturated ammonium chloride solution. The organic layer is separated, diluted with benzene and washed successively with water, ice cold n hydrochloric acid solution, sodium bicarbonate solution and brine. The organic layer is evaporated to dryness and the oil that remains is distilled under vacuum to give 13.57 g. (93.5% of theoretical yield) of 4-benzyl-4-carbomethoxy-1-cyclohexanone ethylene ketal[5] as a viscous oil having a boiling point of 155° to 156° C. at 0.25 mm. of Hg.

Anal. Calcd. for $C_{17}H_{22}O_4$: C, 70.32; H, 7.64. Found: C, 69.94; H, 7.60.

Preparation 5 4-(p-Methylbenzyl)-4-carbomethoxy-1-cyclohexanone ethylene ketal[5]

To a solution of 11.7 g. (0.112 M) of diisopropylamine in 115 ml. of tetrahydrofuran cooled in ice: methanol, 75 ml. of 1.67 n-butyl lithium in pentane is added over the course of about 12 minutes. There is then added, first, 23.1 g. (0.112 M) of 4-carbomethoxy-1-cyclohexanone ethylene ketal[5] (obtained as in Preparation 3) in 115 ml. of tetrahydrofuran in the course of about 15 minutes, and then 14 g. (0.112 M) of α-chloro-p-xylene in 115 ml. of tetrahydrofuran. The mixture is stirred in the cold for about 1 hour and at room temperature for about 2 hours, and then 100 ml. of saturated aqueous ammonium chloride solution and benzene added. The organic layer is separated, washed successively with water, 2.5 N hydrochloric acid solution, water and brine, and then evaporated to dryness. The residue is distilled under vacuum to give 21.47 g. (64% yield) of 4-(p-methylbenzyl)-4-carbomethoxy-1-cyclohexanone ethylene ketal[5] as a viscous oil having a boiling point of 166° to 168.5° C. at 0.3 mm. of Hg.

Anal. Calcd. for $C_{18}H_{24}0_2$: C, 71.02; H, 7.95; M.W. 304. Found: C, 71.23; H, 8.03; m/e 304.

Preparation 6 4-(m-Methylbenzyl)-4-carbomethoxy-1-cyclohexanone ethylene ketal[5]

To a solution of 10.1 g. (0.101 M) of diisopropylamine in 100 ml. of tetrahydrofuran cooled in ice: methanol, 62 ml. of 1.61 n-butyl lithium in pentane is added. There is then added, first 20 g. (0.10 M) of 4-carbomethoxy-1-cyclohexanone ethylene ketal[4] (obtained as in Preparation 3) in 100 ml. of tetrahydrofuran in the course of about 12 minutes, and then 18.5 g. of α-bromo-m-xylene in 100 ml. of tetrahydrofuran in about 12 minutes. The mixture is stirred in the cold for about 1 hour and at room temperature for about 1 hour, and then 100 ml. of saturated ammonium chloride solution and benzene added. The organic layer is separated, washed successively with water, 2.5 N hydrochloric acid solution, water, sodium bicarbonate solution and brine, and then evaporated to dryness. The residue is distilled under vacuum to give 21.32 g. (70% yield) of 4-(m-methylbenzyl)-4-carbomethoxy-1-cyclohexanone ethylene ketal[5] as a viscous oil having a boiling point of 160° to 163° C. at 0.4 mm. of Hg.

Anal. Calcd. for $C_{18}H_{24}O_4$: C, 71.02; H, 7.95; M.W. 304. Found: C, 71.05; H, 8.12; m/e 304.

Preparation 7 4-(m-Methoxybenzyl)-4-carbomethoxy-1-cyclohexanone ethylene ketal[5]

To an ice cooled solution of 10.25 g. (0.102 M) of diisopropylamine in 100 ml. of tetrahydrofuran, 66 ml. of 1.67 n-butyl lithium in pentane is added. There is then added, first, 19.6 g. (0.0995 M) of 4-carbomethoxy-1-cyclohexane ethylene ketal[4] (obtained as in Preparation 3) in 100 ml. of tetrahydrofuran in the course of about 10 minutes, and then 15.3 g. of m-methoxybenzyl chloride in 100 ml. of tetrahydrofuran in about 17 minutes. The mixture is stirred at room temperature for about 2 hours and treated with 100 ml. of saturated ammonium chloride solution and benzene. The organic layer is washed successively with water, 2.5 N hydrochloric acid, water and brine, and then evaporated to dryness. The residue is distilled under vacuum to give 22.32 g. (70% yield) of 4-(m-methoxybenzyl)-4-carbomethoxy-1-cyclohexanone ethylene ketal[5] having a boiling point of 159° to 165° C. at 0.2 mm. of Hg.

Anal. Calcd. for $C_{18}H_{24}O_2$: C, 67.48; H, 7.55. Found: C, 67.71; H, 7.81.

Following the procedures of Preparation 4 through 7 but substituting other halides, such as
1. p-trifluoromethylbenzyl bromide,
2. m-chlorobenzyl bromide,
3. p-propylbenzyl bromide, and the like, yields, respectively,
   1. 4-[p-(trifluoromethyl)benzyl]-4-carbomethoxy-1-cyclohexanone ethylene ketal[5],
   2. 4-(m-chlorobenzyl)-4-carbomethoxy-1-cyclohexanone ethylene ketal[5],
   3. 4-(p-propylbenzyl)-4-carbomethoxy-1-cyclohexanone ethylene ketal[5], and the like.

Preparation 8 1-Benzyl-4-cyclohexanone-1-carboxylic acid[7]

1. A mixture of 16.64 g. (0.057 M) of 4-benzyl-4-carbomethoxy-1-cyclohexane ethylene ketal[5] (prepared as in Preparation 4) and 2.5 g. of potassium hydroxide in 100 ml. ethylene glycol is stirred at reflux for about 16 hours. The mixture is then allowed to cool and diluted with water. The solution is washed once with water and then made strongly acid with concentrated hydrochloric acid. The precipitated gum is extracted with ether and this solution washed first with water, then brine, and evaporated to dryness to give 4-benzyl-4-carboxy-1-cyclohexanone ethylene ketal[6].

2. A solution of the residue[6] and 13 ml. of 2.5 N hydrochloric acid in 130 ml. of acetone is stirred at room temperature for about 20 hours, most of the solvent removed under vacuum and the residue dissolved in ether. The organic layer is washed with water and brine and evaporated to dryness. The residual gum is chromatographed on a column of 800 ml. of acid washed silica gel with elution by 4% acetic acid in methylene chloride. The crystalline fractions are combined and recrystallized twice from methylene chloride: cyclohexane to give 5.62 g. (42% yield) of 1-benzyl-4-cyclohexanone-1-carboxylic acid[7] having a melting point of 120° to 123° C.

Anal. Calcd. for $C_{14}H_{16}O_2$: C, 72.39; H, 6.94. Found: C, 72.24; H, 6.86.

Preparation 9
1-(p-Methoxybenzyl)-4-cyclohexanone-1-carboxylic acid[7]

1. A mixture of 21.47 g. (0.0706 M) of 4-(p-methoxybenzyl)-4-carbomethoxy-1-cyclohexanone ethylene ketal[5] (prepared in Preparation 5) and 2.5 g. of potassium hydroxide in 100 ml. of ethylene glycol is stirred at reflux for about 16 hours. The mixture is then allowed to cool and diluted with water. The solution is washed once with water and then made strongly acidic with concentrated hydrochloric acid. The precipitated gum is extracted with ether and this solution washed with brine and evaporated to dryness to give 4-(p-methoxybenzyl)-4-carboxy-1-cyclohexanone ethylene ketal[6].

2. A solution of the residue[6] and 25 ml. of 2.5 N hydrochloric acid in 200 ml. of acetone is stirred at room temperature for about 24 hours, most of the solvent is removed under vacuum and the residue dissolved in ether. The organic layer is washed with brine and evaporated to dryness. The residue is chromatographed on a column of 1500 ml. of silica gel with elution by 3% acetic acid in methylene chloride. The crystalline fractions are combined to give 6.8 g. (39% yield) of 1-(p-methoxybenzyl)-4-cyclohexanone-1-carboxylic acid[7] as a waxy solid. A small sample is recrystallized from ether: petroleum ether to give crystals[7] having a melting point of 120° to 123° C.

Anal. Calcd. for $C_{15}H_{18}O_3$: C, 73.14; H, 7.37. Found: C, 73.20; H, 7.60.

Preparation 10
1-(m-Methylbenzyl)-4-cyclohexanone-1-carboxylic acid[7]

1. A solution of 21.31 g. (0.0701 M) of 4-(m-methylbenzyl)-4-carbomethoxy-1-cyclohexanone ethylene ketal[5] (prepared in Preparation 6) and 3.4 g. of potassium hydroxide in 140 ml. of ethylene glycol is heated at reflux for about 20 hours. The mixture is then allowed to cool, diluted with water and extracted with ether. The aqueous layer is then made strongly acidic and the precipitated gum extracted with ether. This extract is washed with water and brine and evaporated to dryness to yield 4-(m-methylbenzyl)-4-carboxy-1-cyclohexanone ethylene ketal[6].

2. A solution of the residue[6] and 25 ml. of 2.5 N hydrochloric acid in 200 ml. of acetone is stirred at room temperature for about 16 hours, the solvent removed under vacuum and the residue extracted with ether. The extract is washed with water and brine and evaporated to dryness. The residue is chromatographed on 2000 ml. of acid washed silica gel with elution by 4% acetic acid in methylene chloride. The fractions found similar by thin layer chromatography are combined to give 14.8 g. (56% yield) of 1-(m-methylbenzyl)-4-cyclohexanone-1-carboxylic acid[7] as a waxy solid.

Preparation 11
1-(m-Methoxybenzyl)-4-cyclohexanone-1-carboxylic acid[7]

1. A mixture of 24.3 g. (0.076 M) of 4-(m-methoxybenzyl)-4-carbomethoxy-1-cyclohexanone ethylene ketal[5] (prepared as in Preparation 7) and 4.35 g. of sodium hydroxide in 155 ml. of ethylene glycol is heated at reflux for about 42 hours. The mixture is then diluted with water and washed with ether. The organic layer is made acidic with hydrochloric acid the precipitated gum dissolved in ether. The ether solution is washed with brine and evaporated to dryness to give 4-(m-methoxybenzoyl)-4-carboxy-1-cyclohexanone ethylene ketal[6].

2. A solution of the residue and 27 ml. of 2.5 N hydrochloric acid in 220 ml. of acetone is allowed to stand at room temperature for about 18 hours, then most of the solvent removed under vacuum and the residue dissolved in ether. The organic layer is washed with brine and evaporated to dryness. The residue is chromatographed on a column of acid washed silica gel with elution first by 0.5% acetic acid: methylene chloride then 2% acetic acid: methylene chloride. Those fractions found similar by thin layer chromatography are combined, the solvent evaporated and the resulting solid recrystallized twice from ether: Skellysolve B to give 7.18 g. (36% of theoretical yield) of 1-(m-methoxybenzyl)-4-cyclohexanone-1-carboxylic acid[7] having a melting point of 109° to 112.5° C. An additional 3.82 g. (19% yield) of product [7] melting at 109° to 111° C. is obtained from the mother liquor.

Anal. Calcd. for $C_{15}H_{16}O_4$: C, 68.68; H, 6.92. Found: C, 68.30; H, 6.92.

Following the procedures of Preparation 8 through 11 but substituting other 4-benzyl-4-carbomethoxy-1-cyclohexanone ethylene ketals[5] as starting materials, such as 1. 4-(o-methylbenzyl)-4-carbomethoxy-1-cyclohexanone ethylene ketal[5], yields, 1. 1-(o-methylbenzyl)-4-cyclohexanone-1-carboxylic acid[7].

Preparation 12
Spiro(cyclohexane-1,2'-indan)-1',4-dione[8]

To 100 ml. of freshly distilled hydrogen fluoride, (14.63 M) of 1-benzyl-4-cyclohexanone-1-carboxylic acid[7] (prepared as in Preparation 8) is added. The solution is allowed to stand at room temperature for about 18 hours and then poured cautiously into saturated aqueous sodium bicarbonate solution. The precipitated gum is extracted with benzene. The organic layer is washed successively with water, aqueous sodium bicarbonate solution and brine, and then evaporated to dryness. The residue is chromatographed on a column of 1500 ml. of silica gel with elution by 20% acetone in Skellysolve B. There is first obtained a small amount of by-product followed by 10.5 g. (78%) of spiro(cyclohexane-1,2'-indan)-1',4-dione[8], having a melting point of 70.5° to 72° C.

Anal. Calcd. for $C_{14}H_{14}O_2$: C, 78.48; H, 6.59. Found: C, 78.43; H, 6.59.

The less polar by-product is recrystallized from petroleum ether to give 0.28 g. of a compound, which in view of its mass spectrum and elemental analysis is spiro(cyclohexane-1,2'-indan)-4,4-difluoro-1'-one.

Preparation 13
6'-Methylspiro(cyclohexane-1,2'-indan)-1',4-dione[8]

To 50 ml. of freshly distilled hydrogen fluoride, 6.8 g. (0.026 M) of 1-(p-methylbenzyl)-4-cyclohexanone-1-carboxylic acid[7] (prepared in Preparation 9) is added. The solvent is allowed to evaporate over a period of about 3 days. The residue is dissolved in ether and this solution washed successively with water, aqueous sodium bicarbonate solution and brine. The solution is evaporated to dryness and the gum that remains is chromatographed on a column of 700 ml. of silica gel with elution by 20% acetone: Skellysolve B. The fractions found similar by thin layer chromatography are combined and rechromatographed on a column of 400 ml. of silica gel with elution by 20% acetone: Skellysolve B. The crystalline fractions are combined and recrystallized from acetone: Skellysolve B to give 2.06 g. (35% yield) of 6'-methylspiro(cyclohexane-1,2'-indan)-1',4-dione[8] having a melting point of 110° to 113° C.

Anal. Calcd. for $C_{15}H_{16}O_2$: C, 78.92; H, 7.06; M.W. 228. Found: C, 78.92; H, 7.13; m/e 228.

Preparation 14
5'-Methylspiro(cyclohexane-1,2'-indan)-1',4-dione[8]

Onto 14.8 g. (0.060 M) of 1-(m-methylbenzyl)-4-cyclohexanone-1-carboxylic acid[7] (prepared in Preparation 10) 100 ml. of hydrogen fluoride is distilled. Following about 2 days of standing at room temperature the solution is poured into saturated aqueous sodium bicarbonate solution. The precipitate is dissolved in ether and the organic layer is washed successively with water, saturated aqueous sodium bicarbonate solution and brine and evaporated to dryness. The residue is chromatographed on a column of 1200 ml. of Florisil with elution by 10% acetone: Skellysolve B. The crystalline fractions are combined and recrystallized from acetone: Skellysolve B to give 7.3 g. (53% yield) of 5'-methylspiro(cyclohexane-1,2'-indan)1',4-dione[8] having a melting point of 121° to 122.5° C.

Anal. Calcd. for $C_{15}H_{16}O_2$: C, 78.92; H, 7.01. Found: C, 78.79; H, 7.22.

Preparation 15
5'-Methoxyspiro(cyclohexane-1,2'indan)1',4-dione[8]

A suspension of 15.63 g. (0.060 M) of 1-(m-methoxybenzyl)-4-cyclohexanone-1-carboxylic acid [7] (prepared as in Preparation 11) and 12.5 g. of phosphorus pentachloride in 190 ml. of monochlorobenzene is stirred mechanically under reflux for about 1.5 hours and at room temperature for about 1.5 hours. The mixture is then cooled in ice and treated with 6.85 ml. of stannic chloride. After about 0.5 hours of stirring in the cold and about 18 hours at room temperature, 96 ml. of 2.5 N hydrochloric acid is added in the course of about 10 minutes. After about an additional hour of stirring, the organic layer is separated, washed successively with water, aqueous sodium bicarbonate solution and brine and evaporated to dryness. The residue is chromatographed on a column of 1200 ml. of silica gel with elution by 10% ethyl acetate in methylene chloride. The crystalline fractions are combined to give 7.51 g. (51% yield) of 5'-methoxyspiro[cyclohexane-1,2'-indan)-1',4-dione[8] having a melting point of 105° to 107° C., and an analytic sample melting at 110° to 112° C.

Anal. Calcd. for $C_{15}H_{16}O_3$: C, 73.75; H, 6.60; M.W. 244. Found: C, 73.75; H, 6.65; m/e 244.

Following the procedures of Preparation 12 through 15 but substituting other 1-benzyl-4-cyclohexanone-1-carboxylic acids[7] as starting materials, such as 1-(p-ethylbenzyl)-4-cyclohexanone-1-carboxylic acid[7], and the like, yields, 6'-ethylspiro(cyclohexane-1,2'-indan)-1',4-dione[8], and the like.

Preparation 16
Spiro(cyclohexane-1,2'-indan)-1',4-dione 4-ethylene ketal[9]

A mixture of 1.77 g. (0.0083 M) of spiro(cyclohexane1,2'-indan)-1',4-dione[8] (prepared as in Preparation 12) 0.51 g. (0.46 ml., 0.0082 M) of ethylene glycol and 0.1 g. of p-toluenesulfonic acid in 50 ml. of benzene is heated at reflux under a Dean-Stark trap for about 4 hours. The mixture is allowed to cool, washed successively with aqueous sodium bicarbonate solution, water and brine and evaporated to dryness. The residual solid is recrystallized from cyclohexane to give 1.67 g. (75% yield) of spiro(cyclohexane-1,2'-indan)-1',4-dione 4-ethylene ketal[9], having a melting point of 158 to 160.5° C.; $v_{max}$. 1690 $cm^{-1}$.

Anal. Calcd. for $C_{16}H_{18}O_3$: C, 74.39; H, 7.02 M.W. 258. Found: C, 73.99; H, 6.98; m/e 258.

Preparation 17
5'-Methylspiro(cyclohexane-1,2'-indan)1',4-dione 4-ethylene ketal[9]

A mixture of 2.06 g. (0/00905 M) of 5'-methylspiro(-cyclohexane-1,2'-indan)-1',4-dione[8] (prepared in Preparation 14), 0.56 g. (0.50 ml.) of ethylene glycol and 0.1 g. of p-toluenesulfonic acid in 50 ml. of benzene is heated at reflux under a Dean-Stark trap for about 2 hours. The mixture is allowed to cool, washed with aqueous sodium bicarbonate solution then water and evaporated to dryness. The residual solid is recrystallized from methylene chloride: cyclohexane to give 1.96 g. (86%) of 5'-methylspiro(cyclohexane-1,2'-indan)-1',4-dione 4-ethylene ketal[9], melting at 124° to 127° C.

Anal. Calcd. for $C_{17}H_{20}O_3$: C, 74.97; H, 7.40. Found: C, 74.97; H, 7.51.

Preparation 18
6'-Methylspiro(cyclohexane-1,2'-indan)1',4-dione 4-ethylene ketal[9]

A mixture of 7.3 g. (0.032 M) of 6'-methylspiro(cyclohexane-1,2'-indan)-1',4-dione[8] (prepared in Preparation 13), 2.15 g. (1.95 ml.) of ethylene glycol and 0.5 g. of p-toluene sulfonic acid in 200 ml. of benzene is heated at reflux under a Dean-Stark trap for about 5 hours. The mixture is allowed to cool, washed successively with aqueous sodium bicarbonate solution, water and brine and evaporated to dryness. The residual solid is recrystallized from methylene chloride: Skellysolve B to give 7.94 g. (91% yield) of 6'-methylspiro(cyclohexane-1,2'-indan)-1',4-dione 4-ethylene ketal[9] melting at 116° to 118° C.

Anal. Calcd. for $C_{17}H_{20}O_3$: C, 74.97; H, 7.40. Found: C, 75.33; H, 7.65.

Preparation 19
5'-Methoxyspiro(cyclohexane-1,2'-indan)-1',4-dione 4-ethylene ketal[9]

A mixture of 4.89 g. (0.0196 M) of 5'-methoxyspiro(cyclohexane-1,2'-indan)-1',4-dione[8] (prepared as in Preparation 15), 1.21 g. of ethylene glycol and 0.2 g. of p-toluenesulfonic acid in 100 ml. of benzene is heated at reflux under a Dean-Stark trap for about 5 hours. The mixture is allowed to cool, washed with aqueous sodium bicarbonate solution and evaporated to dryness. The residue is recrystallized twice from methylene chloride: Skellysolve B to give 4.13 g. (73% yield) of 5'-methoxyspiro(cyclohexane-1,2'-indan)-1',4-dione 4-ethylene ketal[9] having a melting point of 142° to 144° C.

Anal. Calcd. for $C_{17}H_{20}O_4$: C, 70.81; H, 6.99. Found: C, 71.06; H, 7.19.

Following the procedures of Preparation 16 through 19 but substituting other spiro(cyclohexane-1,2'-indan)-1',4-diones[8] as starting materials, such as
1. 7'-(trifluoromethyl)spiro(cyclohexane-1,2'-indan)-1',4-dione[8],
2. 5'-ethoxyspiro(cyclohexane-1,2'-indan)-1',4-dione[8], and the like,
yields, respectively,
1. 7'-(trifluoromethyl)spiro(cyclohexane-1,2'-indan)-1',4-dione 4-ethylene ketal[9],
2. 5'-ethoxyspiro(cyclohexane-1,2'-indan)-1',4-dione 4-ethylene ketal[9], and the like.

Preparation 20 Spiro(cyclohexane-1,2'-indan)-4-one ethylene ketal[10]

A mixture of 5 g. (0.0194 M) of spiro(cyclohexane1,2'-indan)-1',4-dione 4-ethylene ketal[9] (prepared as in Preparation 16) 2.6 ml. of hydrazine hydrate and 3.76 g. of potassium hydroxide in 50 ml. of ethylene glycol is heated at reflux for about 1.5 hours. Material is then removed by distillation to bring the pot temperature to 200° C. After about 5 hours of additional heating at reflux, the mixture is allowed to cool and diluted with water. The precipitated solid is collected on a filter, dried and recrystallized from petroleum ether to give 4 g. (85% yield) of spiro(cyclohexane-1,2'-indan)-4-one ethylene ketal[10], having a melting point of 70° to 74° C.

Anal. Calcd. for $C_{16}H_{20}O_2$: C, 78.65; H, 8.25. Found: C, 78.39; H, 8.19.

Preparation 21
5'-Methylspiro(cyclohexane-1,2'-indan)4-one ethylene ketal[10]

A mixture of 7.3 g. (0.027 M) of 5'-methylspiro(cyclohexane-1,2'-indan)-1',4-dione 4-ethylene ketal[9] (prepared as in preparation 17), 3.8 ml. of hydrazine hydrate and 5.52 g. of potassium hydroxide in 70 ml. of ethylene glycol is heated at reflux for about 1 hour. Material is then removed by distillation to brig the pot temperature to 200° C. Following about 18 hours of heating at reflux the mixture is allowed to cool and poured into water and extracted with ether. The organic extract is washed with water and brine and evaporated to dryness, to give 5'-methylspiro(cyclohexane-1,2'-indan)-4-one ethylene ketal [10].

Preparation 22
6'-Methylspiro(cyclohexane-1,2'-indan4-one ethylene ketal[10]

A mixture of 7.3 g. (0.027 M) of 6'-methylspiro(cyclohexane-1,2'-indan)-1',4-dione-4-ethylene ketal[9] (prepared as in Preparation 18), 3.8 ml. of hydrazine hydrate and 5.52 g. of potassium hydroxide in 70 ml. of ethylene glycol is heated at reflux for about 1 hour. Material is then removed by distillation to bring the pot temperature to 200° C. Following about 18 hours of heating at reflux the mixture is allowed to cool and poured into water. The precipitated oil is extracted with ether. This organic extract is washed with water and brine and evaporated to dryness, to give 7.01 g. (about 99% yield) of 6'-methylspiro(cyclohexane-1,2'-indan)-4-one ethylene ketal[10] having a melting point of 37° to 41° C. This material, having a nuclear magnetic resonance (NMR) spectrum in agreement with the expected structure, is not satisfactorily recrystallized.

Preparation 23
5'-Methoxyspiro(cyclohexane-1',2-indan)-4-one ethylene ketal[10]

A mixture of 4.57 g. (0.0158 M) of 5'-methoxyspiro(cyclohexane-1,2'-indan)-1',4-dione 4-ethylene ketal[9] (prepared as in Preparation 19), 2.45 g. of hydrazine hydrate and 3.15 g. of potassium hydroxide in 40 ml. of ethylene glycol is heated at reflux for about 1 hour. Solvent is removed by distillation to bring the reaction mixture to 200° C. Following about 1.5 hours at this temperature the mixture is poured into water and is well extracted with ether. The ether extracts are combined and evaporated to dryness. The residue is chromatographed on a 250 ml. column of silica gel with elution by 10% acetone in Skellysolve B to give 2.07 g. (48% yield) of 5'-methoxyspiro(cyclohexane-1',2-indan)-4-one ethylene ketal [10] having a melting point of 59° to 61° C. The analytical sample from an earlier experiment melted at 65° to 66.5° C.

Anal. Calcd. for $C_{17}H_{22}O_3$: C, 74.22; H, 8.08. Found: C, 74.57; H, 8.24.

The aqueous portion (i.e., not extracted by ether), above, is "acidified" with solid carbon dioxide. The precipitated solid is collected on a filter and recrystallized from methanol to give 0.51 g. of by-product, 5''-hydroxydispiro[1,3-dioxolane-2,1'-cyclohexane-4',2''-indan]-1--one hydrazone, having melting ranges of 243° to 246° C. and 285° to 290° C.

Anal. Calcd. for $C_{16}H_{20}N_2O_3$: C, 66.69; H, 6.99; N, 9.71; M.W. 288. Found: C, 66.16; H, 7.14; N, 9.96; m/e 288.

Following the procedures of Preparation 20 through 23 but substituting other spiro(cyclohexane-1,2'-indan)1',4-dione 4-ethylene ketals[9] as starting materials, such as 5'-chlorospiro(cyclohexane-1,2'-indan)-1',4-dione 4-ethylene ketal[9], and the like, yields, 5'-chlorospiro(cyclohexane-1,2'-indan)-4-one ethylene ketal[10], and the like.

Preparation 24 Spriolcyclohexane-1,2'-indan)-4-one [IIA]

A mixture of 4 g. (0.016 M) of spiro(cyclohexane-1,2'-indan)-4-one ethylene ketal[10] (prepared as in Preparation 20) and 8 ml. of 2.5 N hydrochloric acid in 80 ml. of acetone is heated at reflux for about 4 hours. Most of the solvent is removed under vacuum and ether added. The organic layer is separated, washed with water and brine and evaporated to dryness. The residue is chromatographed on a 350 ml. column of silica gel with elution by methylene chloride. Those fractions similar by thin layer chromatography are combined to give spiro(cyclohexane-1,2'indan)-4-one[IIA].

Following the procedure of Preparation 24 but substituting other spiro(cyclohexane-1,2'-indan)-4-one ethylene ketals[10] as starting materials, such as 1. 4'-bromospiro(cyclohexane-1,2'-indan)-4-one, ethylene ketal[10],
2. 5'-ethylspiro(cyclohexane-1,2'-indan)-4-one, ethylene ketal[10],
3. 5'-methoxyspiro(cyclohexane-1,2'-indan)-4-one, ethylene ketal[10], and the like, yields, respectively, 1. 4'-bromospiro(cyclohexane-1,2'-indan)-4-one[IIA],
2. 5'-ethylspiro(cyclohexane-1,2'-indan)-4-one[IIA],
3. 5'-methoxyspiro(cyclohexane-1,2'-indan)-4-one [IIA], and the like.

Preparation 25
1'-Hydroxyspiro(cyclohexane-1,2'-indan)-4-one ethylene ketal[11]

A solution of 0.01 M of spiro(cyclohexane-1,2'-indan)-1',4-dione, 4-ethylene ketal[9] (prepared as in Preparation 16) in 50 ml. of tetrahydrofuran is added to a well stirred suspension of 0.5 g. of lithium aluminum hydride in 10 ml. of tetrahydrofuran. The mixture is stirred at room temperature for about 5 hours, cooled in ice and treated successively with 0.5 ml. of water, 0.5 ml. of 15% aqueous sodium hydroxide solution and 1.5 ml. of water. The inorganic gel is removed by filtration and the filtrate evaporated to dryness. The residue is recrystallized from cyclohexane to give 2.45 g. (95%) of 1'-hydroxyspiro)cycohexane-1,2'-indan)-4-one ethylene ketal[11], having a melting point of 125° to 128° C.

Anal. Calcd. for $C_{16}H_{20}O_3$: C, 73.82; H, 7.74 Found: C, 73.48; H, 7.78.

Following the procedure of Preparation 25 but substituting other spiro(cyclohexane-1,2'-indan)-1,4-dione alkylene ketals[9] as starting materials, such as 5'-methoxyspiro(cyclohexane-1,2'-indan)-1',4-dione,4-ethylene ketal[9] yields, 1'-hydroxy-5'-methoxyspiro(cyclohexane-1,2'-indan)4-one ethylene ketal[11].

Preparation 26
1'-hydroxyspiro(cyclohexane-1,2'-indan)-4-one[IIB]

A solution of 2.45 g. (0.0094 M) of 1'-hydroxyspiro(cyclohexane-1,2'-indan)-4-one ethylene ketal[11] (prepared in Preparation 25) and 5 ml. of 2.5 N hydrochloric acid in 50 ml. of acetone is allowed to stand for about 17 hours at room temperature. Most of the solvent is removed under vacuum and the residue dissolved in water and ether. The organic layer is washed with water and brine and evaporated to dryness to give 1'-hyroxyspiro(cyclohexane-1,2'-indan)-4-one[IIB].

Following the procedure of Preparation 26 but substituting other 1'-hydroxyspiro(cyclohexane-1,2'-indan)-4-one alkylene ketal [11] as starting material, such as 1'-hydroxy-5'-ethylspiro(cyclohexane-1,2'-indan)-4-one ethylene ketal[11], and the like. yields, respectively, 1'-hydroxy-5'-ethylspiro(cyclohexane-1,2'-indan)-4-one[IIB], and the like.

Preparation 27
1'-Hydroxy-1'-methylspiro(cyclohexane-1,2'-indan)-4-one ethylene ketal[12]

A solution of 5 g. (0.019 M) of spiro(cyclohexane-1,2'-indan)-1',4-dione 4-ethylene ketal [9] (prepared as in Preparation 16) in 60 ml. of tetrahydrofuran is added to 67 ml. of 3M methyl magnesium bromide in ether. After standing for about 17 hours at room temperature, the mixture is cooled in ice and treated cautiously with 50 ml. of saturated ammonium chloride. The organic layer is separated, diluted with benzene and washed with water and brine. The solution is evaporated to dryness and recrystallized from methylene chloride: cyclohexane to give 3.7 g. (71%) of 1'-hydroxy-1'-methylspiro(cyclohexane-1,2'-indan)-4-one ethylene ketal[12] melting at 140° to 143° C.

Anal. Calcd for $C_{17}H_{22}O_3$: C, 74.47; H, 8.08. Found: C, 74.21; H, 8.09.

Following the procedure of Preparation 27 but substituting other spiro(cyclohexane-1,2'-indan)-1',4-dione 4-ethylene ketals[9] as starting materials, such as 4'-ethoxyspiro(cyclohexane-1,2'-indan)-1',4-dione ethylene ketal[9], yields, 4'-ethoxy-1'-hydroxy-1'-methylspiro(cyclohexane-1,2'-indan)-4-one ethylene ketal[12]

Preparation 28
1'-Exo-methylenespiro(cyclohexane-1,2'-indan)-4-one[IIC]

A solution of 9.82 g. (0.036 M) of 1'-hydroxy-1'-methylspiro(cyclohexane-1,2'-indan)-4-one ethylene ketal [12] (prepared as in Preparation 27) and 25 ml. of 2.5 N hydrochloric acid in 250 ml. of acetone is stirred at room temperature for about 17 hours. The solvent is then removed under vacuum and the residue dissolved in ether and water. The organic layer is washed with water and brine and evaporated to dryness. The residue is recrystallized from petroleum ether to give 5.12 g. (67%) of 1'-exo-methylenespiro(cyclohexane-1,2'-indan)-4-one[IIC], having a melting point of 60° to 62° C. The NMR spectrum of this compound is in agreement with its expected structure.

Following the procedure of Preparation 28 but substituting other 1'-hydroxy-1'-methylspiro(cyclohexane-1,2'-indan)-4-one ethylene ketals[12] as starting materials, such as
6'-chloro-1'-hydroxy-1'-methylspiro(cyclohexane-1,2'-indan)-4-one ethylene ketal[12], yields,
6'-chloro-1'-exo-methylenespiro(cyclohexane-1,2'-indan)-4-one[IIC].

Preparation 29
4-Benzyl-4-hydroxymethylcyclohexane-1-one ethylene ketal(1)

A solution of 22.3 g. (0.77 M) of 4-benzyl-4-carbomethoxy-1-cyclohexaneone ethylene ketal[5] (prepared as in Preparation 4) in 220 ml. of tetrahydrofuran is added to 3 g. of lithium aluminum hydride in 30 ml. of tetrahydrofuran. The mixture is stirred at reflux temperature for about 5.5 hours and then cooled in ice. There is added successively 3 ml. of water, 3 ml. of aqueous 15% sodium hydroxide solution and 9 ml. of water. The inorganic gel is collected on a filter and the filtrate evaporated to dryness. The residue is recrystallized from methylene chloride: Skellysolve B to give 18.8 g. (93% yield) of 4-benzyl-4-hydroxymethylcyclohexan-1-one ethylene ketal (1), having a melting point of 76° to 78° C.

Anal. Calcd. for $C_{16}H_{22}O_3$: C, 73.25; H, 8.45. Found: C, 73.08; H, 8.65.

Following the procedure of Preparation 28 but substituting other 4-benzyl-4-carbomethoxy-1-cyclohexanone ethylene ketals[5] as starting materials, such as
1. 4-(p-methylbenzyl)-4-carbomethoxy-1-cyclohexane ethylene ketal [5],
2. 4-(m-methoxybenzyl)-4-carbomethyloxy-1-cyclohexane ethylene ketal [5],
and the like, yields respectively,
1. 4-(p-methylbenzyl)-4-hydroxymethylcyclohexan-1-one ethylene ketal (1),
2. 4-(m-methoxybenzyl)-4-hydroxymethylcyclohexan-1-one ethylene ketal (1), and the like.

Preparation 30
4-Benzyl-4-hydroxymethylcyclohexan-1-one ethylene ketal methanesulfonate(2)

To an ice cold solution of 4-benzyl-4-hydroxymethylcyclohexan-1-one ethylene ketal (1) (prepared in Preparation 29) in 100 ml. of pyridine, 19 ml. of methanesulfonyl chloride is added. After standing in the cold for about 5.5 hours, the mixture is poured into ice: water. The gum that precipitates is extracted with ether. The organic layer is washed successively with water, ice cold 2.5 N hydrochloric acid, water, saturated aqueous sodium bicarbonate solution and brine, and then evaporated to dryness. The residual solid is recrystallized from methylene chloride: Skellysolve B to give 21.1 g. (86%) of 4-benzyl-4-hydroxymethylcyclohexan-1-one ethylene ketal methanesulfonate (2).

Following the procedure of Preparation 30 but substituting other 4-benzyl-4-hydroxymethylcyclohexan-1-one ethylene ketals (1) as starting materials, such as
1. 4-(p-ethoxybenzyl)-4-hydroxymethylcyclohexan-1-one ethylene ketal (1),
and the like, yields, respectively,
1. 4-(p-ethoxybenzyl)-4-hydroxymethylcyclohexan-1-one ethylene ketal methanesulfonate (2), and the like.

Preparation 31 4-Benzylcyclohexan-4-acetic acid-1-one ethylene ketal (4)

1. A mixture of 18.6 g. (0.055 M) of 4-benzyl-4-hydroxymethylcyclohexan-1-one ethylene ketal methanesulfonate (2) (prepared as in Preparation 30) and 18 g. of potassium cyanide in 180 ml. of hexamethylphosphoramide is heated for about 17 hours in an oil bath at about 145° C. The resulting gel is allowed to cool, diluted to 800 ml. with water and extracted with benzene. The organic layer is washed with water and brine and evaporated to dryness. The residue is chromatographed on 1 l. of silica gel and eluted with 25% ethyl acetate in Skellysolve B and the fractions found similar by TLC pooled to give 4-benzyl-4-(cyanomethyl)cyclohexan-1-one ethylene ketal (3).

2. The product (3), obtained in part (1), above, is heated with 14.5 g. of potassium hydroxide in 105 ml. of ethylene glycol for about 17 hours. The mixture is then allowed to cool, diluted with water and washed once with ether. The aqueous layer is then covered with ether and cautiously acidified. The organic layer is separated, washed with brine and evaporated to dryness. The residue is recrystallized from cyclohexane to give 12.3 g. (77%) of 4-benzylcyclohexan-4-acetic acid-1-one ethylene ketal (4), melting at 116° to 118° C. The analytical sample has a melting point of 118° to 120° C.

Anal. Calcd. for $C_{17}H_{22}O_4$: C, 70.32; H, 7.64. Found: C, 70.50; H, 7.83.

Following the procedure of Preparation 31 but substituting other 4-benzyl-4-hydroxymethylcyclohexan-1-one ethylene ketals (2) as starting materials, such as
1. 4-(m-fluorobenzyl)-4-hydroxymethylcyclohexan-1-one ethylene ketal methanesulfonate (2), and the like, yields, respectively,
1. 4-(m-fluorobenzyl)cyclohexan-4-acetic acid-1-one ethylene ketal (4), and the like.

Preparation 32 Benzylcyclohexan-4-acetic acid-1-one (5)

A solution of 12.3 g. of 4-benzylcyclohexan-4-acetic acid-1-one ethylene ketal (4) (prepared in Preparation 31) and 18 ml. of 2.5 N hydrochloric acid in 180 ml. of acetone is stirred at room temperature for about 62 hours. Most of the solvent is removed under vacuum and the residue dissolved in ether and water. The organic layer is washed with water and brine and evaporated to dryness. The residue is recrystallized from ether: Skellysolve B to give 7.94 g. (76%) of 4-benzylcyclohexan-4-acetic acid-1-one (5), having a melting point of 85° to 87° C. The analytical sample has a melting point of 91° to 92° C.

Anal. Calcd. for $C_{15}H_{18}O_3$: C, 73.15; H, 7.37. Found: C, 73.01; H, 7.58.

Following the procedure of Preparation 32 but substituting other 4-benzylcyclohexan-4-acetic acid-1-one ethylene ketals (4) as starting materials, such as
1. 4-(p-ethoxybenzyl)cyclohexan-4-acetic acid-1-one ethylene ketal (4),
2. 4-(m-nitrobenzyl)cyclohexan-4-acetic acid-1-one ethylene ketal (4), and the like,
yields, respectively,
1. 4-(p-ethoxybenzyl)cyclohexan-4-acetic acid-1-one (5), 2. 4-(m-nitrobenzyl)cyclohexan-4-acetic acid-1-one (5),
and the like.

Preparation 33
3',4'-Dihydrospiro[cyclohexane-1,2'(1'H) naphthalene]-4',4-dione(6)

A solution of 6.43 g. (0.026 M) of 4-benzylcyclohexan-4-acetic acid-1-one (5) (prepared as in Preparation 32) in 40 ml. of freshly distilled hydrogen fluoride is allowed to evaporate at room temperature for about 62 hours. The residue is dissolved in methylene chloride and this solution is washed successively with aqueous sodium bicarbonate solution, water and brine. The solution is eva to dryness and chromatographed on a column of 650 ml. of silica gel and eluted with 20% acetone: Skellysolve B. The crystalline fractions are combined and recrystallized from 20% acetone: Skellysolve B to give 1.95 g. (33%) of 3',4'-dihydrospiro[cyclohexane-1,2'(1'H)-naphthalene]-4',4-dione (6), having a melting point of 158° to 160° C.

Anal. Calcd. for $C_{15}H_{16}O$: C, 78.92; H, 7.06; M.W. 228. Found: C, 78.69; H, 7.31, m/e 228.

Following the procedure of Preparation 33 but substituting other 4-benzylcyclohexan-4-acetic acid-1-ones (5) as starting materials, such as
1. 4-(p-methylaminobenzyl)cyclohexan-4-acetic acid-1-one (5),
2. 4-(m-chlorobenzyl)cyclohexan-4-acetic acid-1-one (5), and the like,
yields, respectively,
1. 3',4'-dihydro-6'-methylaminospiro[cyclohexane-1,2'(1'H)-naphthalene]-4',4-dione (6),
2. 3',4'-dihydro-7'-chlorospiro[cyclohexane-1,2'-(1'H)naphthalene]-4,',4-dione (6), and the like.

Preparation 34
3',4'-Dihydrospiro[cyclohexane-1,2'(1'H)naphthalene]-4',4-dione, 4-ethylene ketal (7)

A mixture of 2.65 g. (0.012 M) of 3',4'-dihydrospiro[cyclohexane-1,2'(1'H)-naphthalene]-4',4-dione (6) (prepared as in Preparation 33), 0.72 g. (0.65 ml.) of ethylene glycol and 0.20 g. of p-toluenesulfonic acid in 100 ml. of benzene is heated at reflux under a Dean-Stark trap for about 14 hours. The mixture is allowed to cool, washed with aqueous sodium bicarbonate solution and brine and evaporated to dryness. The residue is chromatographed on a 300 ml. column of silica gel and eluted with 25% ethyl acetate: Skellysolve B to give 2.2 g. (70%) of 3',4'-dihydrospiro[cyclohexane-1,2'-(1'H)-naphthalene]4',4-dione, 4-ethylene ketal (7), melting at 90° to 91.5° C.

Anal. Calcd. for $C_{17}H_{20}O_3$: C, 74.97; H, 7.40. Found: C, 75.00; H, 7.66.

Following the procedure of Preparation 34 but substituting other 3',4'-dihydrospiro[cyclohexane-1,2'-(1'H)-naphthalene]-4',4-diones (6) as starting materials, such as
1. 3',4'-dihydro-5'-propoxyspiro[cyclohexane-1,2'(-1'H)-naphthalene]-4',4-dione (6),
2. 3',4'-dihydro-6'-ethylspiro[cyclohexane-1,2'-(1'H)-naphthalene]-4',4-dione (6), and the like,
yields, respectively.
1. 3',4'-dihydro-5'-propoxyspiro[cyclohexane-1,2'-(1'H)-naphthalene]-4',4-dione, 4-ethylene ketal (7),
2. 3',4'-dihydro-6'-ethylspiro[cyclohexane-1,2'-(1'H)-naphthalene]-4',4-dione, 4-ethylene ketal (7), and the like.

Preparation 35
3',4'-Dihydrospiro[cyclohexane-1,2'(1'H)-naphthalene]-4-one, ethylene ketal (8)

A mixture of 2.2 g. (0.0081 M) of 3',4'-dihydrospiro[cyclohexane-1,2'(1'H)-naphthalene]-4',4-dione, 4-ethylene ketal (7) (prepared in Preparation 34), 1.2 ml. of hydrazine hydrate and 1.6 g. of potassium hydroxide, is heated at reflux for about 1 hour. Solvent is removed by distillation to bring the temperature of the reaction mixture to about 200° C., and the refluxing is continued for about 17 hours. The mixture is then poured into water and extracted with ether. The organic layer is washed with water and brine and evaporated to dryness. The residue is recrystallized from petroleum ether to give 1.86 g. (88%) of 3',4'-dihydrospiro[cyclohexane-1,2'(1'H)-naphthalen]-4-one, ethylene ketal (8), having a melting point of 79° to 81° C.

Anal. Calcd. for $C_{17}H_{22}O_2$: C, 79.03; H, 8.59. Found: C, 79.14; H, 8.72.

Following the procedure of Preparation 35 but substituting other 3',4'-dihydrospiro[cyclohexane-1,2'(-1'H)-napthalen]-4',4-dione, 4-(ethylene ketals) (7) as starting materials, such as
3',4'-dihydro-7'-nitrospiro[cyclohexane-1,2'(1'H)-naphthalen]-4',4-dione, 4-[(2,2-dimethyltrimethylene)ketal] (7) yields,
3',4'-dihydro-7'-nitrospiro[cyclohexane-1,2'(1'H) naphthalene]-4-one, [(2,2-dimethyltrimethylene)-ketal] (8).

Preparation 36
3',4'-Dihydrospiro[cyclohexane-1,2'(1'H)naphthalen]-4-one (11D)

1. A mixture of 1.86 g. (0.0072 mole) of 3',4'-dihydrospiro[cyclohexane-1,2'(1'H)-naphthalen]-4-one, ethylene ketal (8) (prepared in Preparation 35) and 2 ml. of 2.5 N hydrochloric acid in 40 ml. of acetone is heated at reflux for about 17 hours. Most of the solvent is removed under vacuum and the residue dissolved in water and ether. The organic layer is washed with water and brine and then evaporated to dryness to give 3',4'-dihydrospiro[cyclohexane-1,2'(1'H)naphthalen]-4-one (11D).

Following the procedure of Preparation 36 but substituting other 3',4'-dihydrospiro[cyclohexane-1,2'(-1'H)-naphthalen]-4-one, ethylene ketals (8) as starting materials, such as
3',4'-dihydro-6'-fluorospiro[cyclohexane-1,2'(1'H)-naphthalen[-4-one, 2,2-(dimethyltrimethylene)ketal (8), yields,
3',4'-dihydro-6'-fluorospiro[cyclohexane-1,2'(1'H)-naphthalen]-4-one (11D).

Preparation 37
3',4'-dihydro-4'-hydroxyspiro[cyclohexane-1,2'(1'H)-naphthalen]-4-one (11E)

A solution of 0.01 M of 3',4'-dihydro[cyclohexane-1,2'(1'H)-naphthalene]-4',4-dione, 4-ethylene ketal (7) (prepared as in Preparation 34) in about 50 ml. of tetrahydrofuran is added to a well stirred suspension of 0.5 g. of lithium aluminum hydride in 10 ml. of tetrahydrofuran. The mixture is stirred at room temperature for about 5 hours, cooled in ice and treated successively with 0.5 ml. of water, 0.5 ml. of 15% aqueous sodium hydroxide solution and 1.5 ml. of water. The mixture is then filtered and the filtrate evaporated to dryness. The residue thus obtained is recrystallized from ethyl acetate/cyclohexane to give 3',4'-dihydro- 4'-hydroxyspiro[cyclohexane-1,2'-(1'H)naphthalen]-4-one, ethylene ketal (9); this is then treated with 5 ml. of 2.5 N hydrochloric acid in 50 ml. of acetone and allowed to stand for about 17 hours at room temperature. Most of the solvent is then removed under vacuum and the residue dissolved in water and ether. The organic layer is washed with water and brine and evaporated to dryness to give 3',4'-dihydro-4'-hydroxyspiro[cyclohexane-1,2'-(1'H)-naphthalen]-4-one (11E).

In like manner the other compounds of formula (7) are likewise converted to the corresponding starting compounds of formula (11E).

Preparation 38
3',4'-dihydro-4'-exo-methylenespiro[cyclohexane-1,2'(1'H)-naphthalen]-4-one (11F)

To an anhydrous etheral solution of n-butyl lithium (0.019 moles) under nitrogen, is added (triphenylmethyl)phosphonium bromide over a 5-minute period. This solution is stirred for 4 hours at room temperature and 3',4'-dihydrospiro[cyclohexane-1,2'(1'H)-naphthalene]-4',4-dione, 4-ethylene ketal (0.019 moles) in 20 ml. of anhydrous ether is added dropwise. The mixture is heated under reflux for 6 to about 24 hours, allowed to cool to room temperature and the precipitate formed removed by filtration. The etheral filtrate is washed with water and dried with anhydrous sodium sulfate. The ether is removed under vacuum to give 3',4'-dihydro-4'-exo-methylenespiro[cyclohexane-1,2'(1'H)-naphthalen]-4-one, ethylene ketal (10) which is then treated with about 25 ml. of 2.5 N hydrochloric acid in 250 ml. of acetone and stirred at room temperature for about 17 hours. The solvent is then removed under vacuum and the residue dissolved in ether and water. The organic layer is washed with water and brine and evaporated to dryness. The residue thus obtained is recrystallized from petroleum ether to give 3',4'-dihydro-4'-exo-methylenespiro[cyclohexane-1,2'(1'H)-naphthalen]-4-one (11F).

In like manner the other compounds of formula (7) are likewise converted to the corresponding starting compounds of formula (11F).

Preparation 39
3-methylspiro[cyclohexane-1,2'-indan]-4-one (11c)

To a solution of 5.09 g. of spiro[cyclohexane-1,2'-indan]-4-one in 100 ml. of boiling benzene containing 0.5 g. of p-toluenesulfonic acid is added 2.0 g. of pyrrolidine. Following 4 hours heating at reflux the resulting solution is concentrated by evaporation to give spiro[cyclohexane-1,2'-indan]-4-one, 4-pyrrolidinyl enamine (11b), which is taken up in dimethylformamide and treated with methyl iodide at about 25° C. for a period of about 16 hours. There is then added 3 ml. of water. Following 3 hours stirring at 25° C. the mixture is then poured into ice-water and extracted with benzene. The extract is washed with water, dilute hydrochloric acid and brine, dried over anhydrous sodium sulfate and concentrated to give a residue which is crystallized from ether petroleum ether to give 3-methylspiro[cyclohexane-1,2'-indan]-4-one (11c).

Preparation 40
3',4'-dihydro-3-ethylspiro[cyclohexane-1,2'-(1'H)-naphthalen]-4-one (11 c).

To a solution of 6.78 g. of 3',4'-dihydrospiro[cyclohexane-1,2'-(1'H)-naphthalen]-4-one in 100 ml. of boiling benzene containing 0.7 g. of p-toluenesulfonic acid is added 2.2 g. of pyrrolidine. The resulting solution is then concentrated by evaporation to give 3',4'-dihydrospiro[cyclohexane-1,2'(1'H)-naphthalen]-4-one, 4-pyrrolidinyl enamine (11b), which is taken up in dimethylformamide and treated with ethyl bromide at about 25° C. for a period of about 18 hours. Water (3 ml.) is then added and the mixture stirred for 3 hours. The mixture is then poured into ice water and extracted with benzene. The extract is washed with water, 2.5 N hydrochloric acid and brine, dried over over anhydrous sodium sulfate and concentrated to give a residue which is crystallized from ether; petroleum ether to give 3',4'-dihydro-3-ethylspiro[cyclohexane-1,2'-(1'H)naphthalen]-4-one (IIc).

In the same manner following the procedures of Preparations 39 and 40 above, other compounds of formula IIa are likewise converted their corresponding 3-alkyl derivatives of formula IIc.

EXAMPLE 1 spiro[cyclohexane-1,2'-indan]-4-one oxime (III)

A mixture of 3.0 g. (0.015 mole) of spiro[cyclohexane-1,2'-indan]-4-one, 3.0 g. of hydroxylamine hydrochloride, 6 ml. of 50% sodium hydroxide solution and 10 ml. of water in 100 ml. of tetrahydrofuran is stirred at reflux for about 5 hours. The mixture is then allowed to cool and the bulk of the solvent removed in vacuum. The solid which is obtained when the residue is diluted with water is recrystallized from cyclohexane to give 3.10 g. (96%) of spiro[cyclohexane-1,2'-indan]-4-one oxime (III), m.p. 120°–122° C.

Anal. Calcd for $C_{14}H_{17}NO$: C, 78.10; H, 7.96; N, 6.51. Found: C, 78.08; H, 7.85; N, 6.50.

Following the procedure of Example 1, other compounds of formula III are prepared by substituting other compounds of formula II as starting materials therein, such as:
1. 4'-bromospiro[cyclohexane-1,2'-indan]-4-one (IIA),
2. 5'-ethylspiro[cyclohexane-1,2'-indan]-4-one (IIA),
3. 5'-methoxyspiro[cyclohexane-1,2'-indan]-4-one (IIA),
4. 1'-hydroxyspiro[cyclohexane-1,2'-indan]-4-one (IIB),
5. 1'-hydroxy-5'-ethylspiro[cyclohexane-1,2'-indan]-4-one (IIB),
6. 1'-exo-methylenespiro[cyclohexane-1,2'-indan]-4-one (IIC),
7. 6'-chloro-1'-exo-methylenespiro[cyclohexane-1,2'-indan]-4-one (IIC),
8. 3-methylspiro[cyclohexane-1,2'-indan]-4-one (IIc);

and the like, to respectively obtain:
1. 4'-bromospiro[cyclohexane-1,2'-indan]-4-one, oxime (III);
2. 5'-ethylspiro[cyclohexane-1,2'-indan]-4-one, oxime (III);
3. 5'-methoxyspiro[cyclohexane-1,2'-indan]-4-one, oxime (III);
4. 1'-hydroxyspiro[cyclohexane-1,2'-indan]-4-one, oxime (III);
5. 1'-hydroxy-5'-ethylspiro[cyclohexane-1,2'-indan]-4-one, oxime (III);
6. 1'-exo-methylenespiro[cyclohexane-1,2'-indan]-4-one, oxime (III);
7. 6'-chloro-1'-exo-methylenespiro[cyclohexane-1,2'-indan]-4-one, oxime (III);

8. 3-methylspiro[cyclohexane-1,2'-indan]-4-one, oxime (III); and the like.

EXAMPLE 2

Spiro[cyclohexane-1,2'-indan]-4-one, 0-(p-tolylsulfonyl)oxime (IV)

p-Toluenesulfonyl chloride (6.73 g.) is added to an ice cooled solution of 7.65 g. (0.0350 mole) of spiro[cyclohexane-1,2'-indan]-4-one, oxime (III) in 50 ml. pyridine. Following 6 hours standing in the cold the mixture is poured into ice water to give 9.96 g. (76%) of spiro[cyclohexane-1,2'-indan]-4-one, 0-(p-tolylsulfonyl)oxime (IV), m.p. 74°–81° C. A sample recrystalized from chloroform: ethyl acetate melted at 98°–99° C.

Anal. Calcd for $C_{21}H_{23}NO_3S$: C, 68.26; H, 6.27; N, 3.97; MW, 369. Found: C, 68.45; H, 6.37; N, 3.66; M/e 369.

Following the procedure of Example 2, but substituting other compounds of formula III as starting materials therein, such as the oximes listed under (I) through (8) in Example 1, above, yields respectively:
1. 4'-bromospiro[cyclohexane-1,2'-indan]-4-one, 0-(p-tolylsulfonyl)oxime (IV);
2. 5'-ethylspiro[cyclohexane-1,2'-indan]-4-one, 0-(p-tolylsulfonyl)oxime (IV);
3. 5'-methoxyspiro[cyclohexane-1,2'-indan]-4-one, 0-(p-tolylsulfonyl)oxime (IV);
4. 1'-hydroxyspiro[cyclohexane-1,2'-indan]-4-one, 0-(p-tolylsulfonyl)oxime (IV);
5. 1'-hydroxy-5'-ethylspiro[cyclohexane-1,2'-indan]-4-one, 0-(p-tolylsulfonyl)oxime (IV);
6. 1'-exo-methylenespiro[cyclohexane-1,2'-indan]-4-one, 0-(p-tolylsulfonyl)oxime (IV);
7. 6'-chloro-1'-exo-methylenespiro[cyclohexane-1,2'-indan]-4-one, 0-(p-tolylsulfonyl)oxime (IV);
8. 3-methylspiro[cyclohexane-1,2'-indan]-4-one, 0-(p-tolylsulfonyl)oxime (IV); and the like.

EXAMPLE 3 2,3,5,6-Tetrahydro spiro[4H-azepine-4,2'-indan]-7-(1H)one (V)

A solution of 9.96 g. (0.269 mole) of spiro[cyclohexane-1,2'-indan]-4-one, 0-(p-tolylsulfonyl)oxime in 100 ml. of acetic acid is heated at reflux for about 6 hours. The mixture is then allowed to cool and poured into water. The precipitate thus obtained is extracted with methylene chloride and the extract washed with sodium bicarbonate. The solid which remains when the extract is taken to dryness is recrystallized from acetone:Skellysolve B hexanes to give 3.97 g. (69% yield) of 2,3,5,6-tetrahydro spiro[4H-azepine-4,2'-indan]-7(1H)-one, m.p. 164°–165° C.

Anal. Calcd for $C_{14}H_{17}NO$: C, 78.09; H, 7.96; N, 6.51; WM, 215. Found: C, 77.85; H, 7.92; N, 6.37; M/e 215.

Following the procedure of Example 3, but substituting other compounds of formula IV as starting materials therein, such as the 0-(p-tolylsulfonyl)oximes listed under (I) through (8) in Example 2, above, yields respectively:
1. 4'-bromo-2,3,5,6-tetrahydro spiro[4H-azepine-4.2'-indan]-7-(1H)-one (V);
2. 5'-ethyl-2,3,5,6-tetrahydro spiro[4H-azepine-4,2'-indan]-7(1H)-one (V);
3. 5'-methoxy-2,3,5,6-tetrahydro spiro[4H-azepine-4,2'-indan]-7(1H)-one (V);
4. 1'-hydroxy-2,3,5,6-tetrahydro spiro[4H-azepine-4,2'-indan]-7(1H)-one (V);
5. 5'-ethyl-1'-hydroxy-2,3,5,6-tetrahydro spiro-[4H-azepine-4,2'-indan]-7(1H)-one (V);
6. 1'-exo-methylene-2,3,5,6-tetrahydro spiro[4H-azepine-4,2'-indan]-7(1H)-one (V);
7. 6'-chloro-1'-exo-methylene-2,3,5,6-tetrahydro spiro[4H-azepine-4,2'-indan]-7(1H)-one (V);
8. 2-methyl-2,3,5,6-tetrahydro spiro[4H-azepine-4,2'-indan]-7(1H)-one (V); and the like.

EXAMPLE 4

1,2,3,5,6,7-Hexahydro spiro [4H-azepine-4,2'-indan], hydrochloride VI

A solution of 2.91 g. (0.014 mole) of 2,3,5,6-tetrahydro spiro[4H-azepine-4,2'indan]-7(1H)-one (V) is added to 0.58 g. lithium aluminum hydride in 30 ml. of tetrahydrofuran. Following 6 hours stirring under reflux, the mixture is cooled in ice and treated in turn with 0.6 ml. of water, 0.6 ml. 15% aqueous sodium hydroxide and 1.8 ml. water. The inorganic gel is collected on a filter and the filtrate taken to dryness. A solution of the residue thus obtained in diethyl ether is treated with N hydrochloric acid in diethyl ether. The precipitated salt thus obtained is recrystallized from methanol: ethyl acetate to give 3.00 g. (90%) 1,2,3,5,6,7-hexahydro spiro[4H-azepine-4,2'-indane], hydrochloride VI, m.p. 235°–237° C.

Anal. Calcd MW 201, M/e 201 (base peak).

Following the procedure of Example 4, but substituting other compounds of formula V as starting materials therein, such as the compounds listed under (I) through (8) in Example 3, above, yields respectively:
1. 4'-bromo-1,2,3,5,6,7-hexahydro spiro[4H-azepine-4,2'-indane], hydrochloride (VI);
2. 5'-ethyl-1,2,3,5,6,7-hexahydro spiro[4H-azepine-4,2'-indane], hydrochloride (VI);
3. 5'-methoxy-1,2,3,5,6,7-hexahydro spiro[4H-azepine-4,2'-indane], hydrochloride (VI);
4. 1'-hydroxy-1,2,3,5,6,7-hexahydro spiro[4H-azepine-4,2'-indane], hydrochloride (VI);
5. 5'-ethyl-1'-hydroxy-1,2,3,5,6,7-hexahydro spiro[4H-azepine-4,2'-indane], hydrochloride (VI);
6. 1'-exo-methylene-1,2,3,5,6,7-hexahydro spiro[4H-azepine-4,2'-indane], hydrochloride (VI);
7. 6'-chloro-1'-exo-methylene-1,2,3,5,6,7-hexahydro spiro[4H-azepine-4,2'-indane], hydrochloride (VI);
8. 2-methyl-1,2,3,5,6,7-hexahydro spiro[4H-azepine-4,2'-indane], hydrochloride (V); and the like.

EXAMPLE 5

1-[3-(Dimethylamino)propyl]-1,2,3,5,6,7-hexahydrospio[4H-azepine-4,2'-indane], dihydrochloride (I)

To a solution of the free base prepared from 1.53 g. (0.0065 mole) of 1,2,3,5,6,7-hexahydro spiro[4H-azepine-4,2'-indane], hydrochloride (VI) in 30 ml. dimethylformamide, there is added 1.08 g. of potassium iodide, 0.90 g. potassium carbonate and 1.57 g. of a 1:1 mixture of 3-chloro-N,N-dimethylpropylamine and toluene. Following 17 hours heating at 90° C. the solvent is removed under vacuum. The residue thus obtained is dissolved in water and benzene. The organic layer is washed with water and brine and taken to dryness. A solution of the residue in methanol is treated with an excess of N-hydrochloric acid in diethyl ether. The mixture is then taken to dryness and the residue recrystallized from methanol: ethyl acetate to give 1.13 g. (50%) of 1-[3-(dimethylamino)propyl]-1,2,3,5,6,7- hexahydrospiro[4H-azepine-4,2'-indane], dihydrochloride (I), m.p. 272°–274° C.

Anal. Calcd for $C_{19}H_{32}Cl_2N_2 \cdot 1/2 H_2O$: C, 61.94; H, 9.03; N, 7.61. Found: C, 62.11; H, 8.69; N, 7.54.

EXAMPLE 6

4'-fluoro-4-[2,3,6,7-tetrahydrospiro[4H-azepine-4,2'-indan]-1(5H)-yl]butyrophenone hydrochloride To a solution of the free base prepared from 1.50 g. (0.0063 mole) of 1,2,3,5,6,7-hexahydro spiro-[4H-azepine-4,2'-indane], hydrochloride (VI); in 40 ml. of dimethylformamide there is added 1.26 g. of potassium iodide, 1.96 g. of potassium carbonate and 1.83 g. of the neopentyl glycol ketal of 4-chloro-4'-fluorobutyrophenone. Following 17 hours heating at 90° C. the solvent is removed in vacuum. The residue is dissolved in water and benzene. The organic layer is washed with water and brine and taken to dryness. A solution of the residue and 7.5 ml. of 15% aqueous sodium hydroxide is allowed to stand at room temperature for about 4 hours. The bulk of the solvent is removed in vacuum. The mixture is washed several times with diethyl ether and then extracted with methylene chloride. The methylene chloride extracts are washed once with N sodium hydroxide and taken to dryness.

The residue thus obtained is chromatographed on 300 ml. silica gel (elution with 5% methanol in methylene chloride saturated with ammonium hydroxide). The fractions which are the same on thin layer chromatography are combined and dissolved in methylene chloride and the solution is washed with 2.5 N hydrochloric acid. The solid which remains when the organic layer is taken to dryness is recrystallized from methylene chloride: ethyl acetate to give 0.90 g. (38%) of 4'-fluoro-4-(2,3,6,7-tetrahydrospiro[4H-azepine-4,2'-indan]-1(5H)-yl)butyrophenone hydrochloride, m.p. 147.5°–150° C.

Anal. Calcd for $C_{24}H_{29}ClFNO$: C, 71.71; H, 2.27; N, 3.48; Cl, 8.82. Found: C, 71.31; H, 7.27; N, 3.50; Cl, 8.51.

Following the procedure of Example 5 and 6 above other compounds of formula VI, for example, those compounds named in under (I) through (8) in Example 4, above, are reacted with a ketal of a haloalkyl aryl ketone or a haloalkyl amine to obtain the corresponding compound of formula I. The following conversions are representative:

1. 4'-bromo-1,2,3,5,6,7-hexahydro spiro[4H-azepine-4,2'-indane] (VI) with 1-chloro-2-(diethylamino)ethane to obtain 1-[2-(diethylamino)ethyl]-4'-bromo-1,2,3,5,6,7-hexahydrospiro[4H-azepine-4,2'-indane], dihydrochloride (I);
2. 5'-ethyl-1,2,3,5,6,7-hexahydro spiro[4H-azepine-4,2'-indane], (VI) with 1-(2-chloroethyl)pyrrolidine to obtain 1-(2-pyrrolidino)ethyl-5'-ethyl-1,2,3,5,6,7-hexahydrospiro[4H-azepine-4,2'-indane], dihydrochloride (I);
3. 5'-methoxy-1,2,3,5,6,7-hexahydro spiro[4H-azepine-4,2'-indane] (VI) with 1-chloro-2-(diethylamino)ethane to obtain 1-[2-(diethylamino)ethyl]-5'-methoxy-1,2,3,5,6,7-hexahydro[4H-azepine-4,2'-indane], dihydrochloride (I),
4. 1'-hydroxy-1,2,3,5,6,7-hexahydro spiro[4H-azepine-4,2'-indane], (VI) with 4-chloro-4'-fluorobutyrophenone neopentyl glycol ketal to obtain 4'-fluoro-4-[1'-hydroxy-2,3,6,7-tetrahydrospiro[4H-azepine-4,2'-indane]-1(5H)-yl]-butyrophenone, hydrochloride (I);
5. 5'-ethyl-1'-hydroxy-1,2,3,5,6,7-hexahydro spiro[4H-azepine-4,2'-indane] (VI) with 1-chloro-2-(dimethylamino)ethane to obtain 1-[2-(dimethylamino)ethyl]-5'-ethyl-1'-hydroxy-1,2,3,5,6,7-hexahydrospiro[4H-azepine-4,2'-indane], dihydrochloride (I);
6. 1'-exo-methylene-1,2,3,5,6,7-hexahydro spiro[4H-azepine-4,2'-indane] (VI) with 1-chloro-3-(diethylamino)propane to obtain 1[3-(diethylamino)propyl]-1'-exo-methylene-1,2,3,5,6,7-hexahydrospiro[4H-azepine-4,2'-indane], dihydrochloride (I);
7. 6'-chloro-1'-exo-methylene-1,2,3,5,6,7-hexahydrospiro[4H-azepine-4,2'-indane] (VI) with 1-(4-chlorobutyl)pyrrolidine to obtain 1-(4-pyrrolidinobutyl)-6'-chloro-1'-exo-methylene-1,2,3,5,6,7-hexahydro spiro[4H-azepine-4,2'-indane], dihydrochloride (I);
8. 2-methyl-1,2,3,5,6,7-hexahydro spiro[4H-azepine-4,2'-indane] (VI) with 1-chloro-2-(diethylamino)ethane to obtain 1-[2-(diethylamino)ethyl]-3-methyl-1,2,3,5,6,7-hexahydro spiro[4H-azepine-4,2'-indane], dihydrochloride (I); and the like.

Other acid addition salts are prepared by substituting the appropriate acid in place of hydrochloric acid.

The free bases of the compounds of formula I are prepared by subjecting the acid addition salt to a base such as potassium carbonate as described in Examples 5 and 6.

EXAMPLE 7

3',4'-dihydrospiro[cyclohexane-1,2'(1'H)naphthalen]-4-one, oxime (III)

A mixture of 8.33 g. (0.039 mole) of 3',4'-dihydrospiro[cyclohexane-1,2'(1'H)naphthalen]-4-one (IID), 5.40 g. hydroxylamine hydrochloride and 10.7 g. potassium carbonate in 100 ml. methanol is heated at reflux for about 6 hours. The solvent is then removed in vacuum and the residue partitioned between methylene chloride and water. The organic layer is washed with water and brine and taken to dryness. The residue is recrystallized from methylene chloride: Skellysolve B hexanes to give 8.52 g. (95%) of 3',4'-dihydrospiro[cyclohexane-1,2'(1'H)naphthalen]-4-one, oxime, m.p. 105°–106.5° C.

Anal. Calcd for $C_{15}H_{19}NO$: C, 78.56; H, 8.35; N, 6.11. Found: C, 78.36; H, 8.31; N, 6.05.

Following the procedure of Example 7, other compounds of formula III are prepared by substituting other compounds of formula II as starting materials therein, such as:

1. 3',4'-dihydro-6'-fluorospiro[cyclohexane-1,2'-(1'H)naphthalen]-4-one (IID);
2. 3',4'-dihydro-4'-hydroxyspiro[cyclohexane-1,2'-(1'H)naphthalen]-4-one (IIE);
3. 3',4'-dihydro-4'-exo-methylenespiro[cyclohexane-1,2'(1'H)naphthalen]-4-one (IIF);
4. 3',4'-dihydro-3-ethylspiro[cyclohexane-1,2'(-1'H)naphthalen]-4-one (IIC); and the like, yields respectively:

1. 3',4'-dihydro-6'-fluorospiro[cyclohexane-1,2'-(1'H)naphthalen]-4-one, oxime (III);
2. 3',4'-dihydro-4'-hydroxyspiro[cyclohexane-1,2'-(1'H)naphthalen]-4-one, oxime (III);
3. 3',4'-dihydro-4'-exo-methylenespiro[cyclohexane-1,2'-(1'H)naphthalen]-4-one, oxime (III);
4. 3',4'-dihydro-3-ethylspiro[cyclohexane-1,2'(-1'H)naphthalen]-4-one, oxime (III); and the like.

EXAMPLE 8

3',4'-dihydrospiro[cyclohexane-1,2'(1'H)naphthalen]-4-one, 0-(p-tolylsulfonyl)oxime (IV)

To an ice cooled solution of 5.96 g. (0.026 mole) of 3',4'-dihydrospiro[cyclohexane-1,2'(1'H)naphthalen]-4-one, oxime (III) in 60 ml. pyridine there is added 5.72 g. p-toluenesulfonyl chloride. Following 6 hours standing in an ice bath, the mixture is poured into ice water. The precipitated solid thus obtained is recrystallized from ether to give 6.02 g. (60%) of 3+,4'-dihydrospiro[cyclohexane-1,2'(1'H)naphthalen]-4-one, 0-(p-toluenesulfonyl)oxime (IV) m.p. 86°–89° C.

Anal. Calcd for $C_{22}H_{25}NO_3S$: C, 68.90; H, 6.57; N, 3.65. Found: C, 68.99; H, 6.55; N, 3.61.

Following the procedure of Example 8, but substituting other compounds of formula (III) as starting materials therein, such as the oximes listed under (1) through (4) in Example 7, above, yields respectively.

1. 3',4'-dihydro-6'-fluorospiro[cyclohexane-1,2'(1'H)naphthalene]-4-one, 0-(p-tolylsulfonyl)oxime (IV);
2. 3',4'-dihydro-4'-hydroxyspiro[cyclohexane-1,2'-(1'H)naphthalene]-4-one, 0-(p-tolylsulfonyl)oxime (IV);
3. 3',4'-dihydro-4'-exo-methylenespiro[cyclohexane-1,2'(1'H)naphthalene]-4-one, 0-(p-tolylsulfonyl)oxime (IV);
4. 3',4'-dihydro-3-ethylspiro[cyclohexane-1,2'(-1'H)naphthalene]-4-one, 0-(p-tolylsulfonyl)oxime (IV); and the like.

EXAMPLE 9

2,3,3',4',5,6-hexahydrospiro[4H-azepine-4,2'-(1'H)-naphthalen]-7-(1H) one (V)

A solution of 5.05 g. (0.013 mole) of 3',4'-dihydrospiro[cyclohexane-1,2'(1'H)naphthalen]-4-one, 0-(p-tolylsulfonyl)oxime (IV) in 50 ml. acetic acid is stirred at reflux for about 24 hours. The mixture is then diluted with water and extracted throughly with benzene. The organic layer is washed with water, saturated aqueous sodium bicarbonate and brine and taken to dryness. The residue is chromatographed over 300 ml. silica gel (elution with 2% methanol: methylene chloride). The crystalline fractions thus obtained are combined to give 2.05 g. (68%) of 2,3,3',5,6-hexahydrospiro[4H-azepine-4,2'(1'H)naphthalen]-7-(1H)-one (V), m.p. 142°–145° C.

Anal. Calcd for $C_{15}H_{19}NO$: C, 78.56; H, 8.38; N, 6.11; M.W. 229. Found: C, 78.52; H, 8.53; N, 6.19; m/e 229.

Following the procedure of Example 9, but substituting other compounds of formula IV as starting materials therein, such as the 0-(p-toluenesulfonyl)oximes listed under (1) through (4) in Example 8, above, yields respectively:

1. 2,3,3',4',5,6-hexahydro-6'-fluorospiro[4H-azepine-4,2'(1'H)naphthalen]-7(1H)-one (V);
2. 2,3,3',4',5,6-hexahydro-4'-hydroxyspiro[4H-azepine-4,2'(1'H)naphthalen]-7(1H)-one (V);
3. 2,3,3',4',5,6-hexahydro-4'-exo-methylenespiro[4H-azepine-4,2'(1'H)naphthalen]-7(1H)-one (V);
4. 2,3,3',4',5,6-hexahydro-2-ethylspiro[4H-azepine-4,2'(1'H)naphthalen]-7-(1H)one (V); and the like.

EXAMPLE 10

1,2,3,3',4',5,6,7-octahydrospiro[4H-azepine-4,2'(-1'H)naphthalene], hydrochloride (VI)

A solution of 2.35 g. (0.010 mole) of 2,3,3',4',5,6-hexahydrospiro[4H-azepine-4,2'(1'H)naphthalen]-7(1H) one (V) in 30 ml. of tetrahydrofuran is added to 0.40 g. lithium aluminum hydride in 10 ml. of tetrahydrofuran. Following 6 hours of stirring at reflux, the mixture is cooled in ice. There is then added in turn 0.4 ml. water, 0.4 ml. 15% sodium hydroxide and 1.2 ml. water. The inorganic gel thus obtained is collected on a filter and the filtrate taken to dryness. The residue thus obtained is dissolved in ether and treated with 10 ml. hydrogen chloride in ether. The precipitated solid thus obtained is recrystallized from methanol: ethyl acetate to give 1.95 g. (74%) of 1,2,3,3',4',5,6,7-octahydrospiro[4H-azepine-4,2'(1'H)naphthalene], hydrochloride (VI) m.p. 205°–207°.

Anal. Calcd for $C_{15}H_{22}ClN$: C, 71.54; N, 8.81; N, 5.56; Found: C, 71.21; N, 8.88; N, 5.53.

Following the procedure of Example 10, but substituting other compounds of formula V as starting materials therein, such as the compounds listed under (1) through (4) in Example 9, above, yields respectively:

1. 1,2,3,3',4',5,6,7-octahydro-6'-fluorospiro[4H-azepine-4,2'(1'H)naphthalene], hydrochloride (VI);
2. 1,2,3,3',5,6,7-octahydro-4'-hydroxyspiro[4H-azepine-4,2'(1'H)naphthalene], hydrochloride (VI);
3. 1,2,3,3',4',5,6,7-octahydro-4'-exo-methylenespiro[4H-azepine-4,2'(1'H)naphthalene], hydrochloride (VI);
4. 1,2,3,3',4',5,6,7-octahydro-2-ethylspiro[4H-azepine-4,2'(1'H)naphthalene], hydrochloride (VI); and the like.

EXAMPLE 11

4'-fluoro-4-[2,3,3',4',6,7-hexahydrospiro-[4H-azepine-4,2'(1'H)naphthalen]-1-(5H)-yl]butyrophenone, hydrochloride (I)

A mixture of the free base obtained from 1.85 g. (0.0074 mole) of 1,2,3,3',4',5,6,7-octahydrospiro[4H-azepine-4,2'(1'H)naphthalene], hydrochloride (VI), 1.47 g. potassium iodide, 2.29 g. potassium carbonate and 2.14 g. of the neopentyl glycol ketal of 4-chloro-p-fluorobutyrophenone in 40 ml. dimethylformamide is stirred for about 17 hours at about 90° C. The solvent is then removed in vacuum and the residue thus obtained is partitioned between benzene and water. The organic layer is washed with water and brine and taken to dryness. A solution of the residue thus obtained and 10 ml. of 2.5 N hydrochloric acid in 20 ml. methanol is stirred at reflux for about 4 hours. The bulk of the solvent is then removed in vacuum and the residue washed twice with ether. The aqueous layer is then extracted several times with methylene chloride. The solid which remains when the methylene chloride extracts are taken to dryness is recrystallized twice from methylene chloride: ethyl acetate to give 1.43 g. (51%) of 4'-fluoro-4-[2,3,3',4',6,7-hexahydrospiro[4H-azepine-4,2'(1'H)-naphthalen]-1-(5H)-yl]butyrophenone, hydrochloride (I), m.p. 170°–171° C.

Anal. Calcd for $C_{25}H_{31}ClFNO$: C, 72.18; H, 7.51; N, 3.37. Found: C, 72.33; H, 7.38; N, 3.29.

Following the procedure of Example 11 (and Examples 5 and 6 above) other compounds of formula VI, for example, those compounds named under (I) through (4) in Example 10 above, are reacted with a ketal of a haloalkyl aryl ketone or a haloalkyl amine to obtain the corresponding compound of formula I, the following conversions are representative:

1. 1,2,3,3',4',5,6,7-octahydro-6'-fluorospiro[4H-azepine-4,2'(1'H)naphthalene] (VI) with the neopentyl ketal of 4-chloro-p-fluorobutyrophenone to obtain 4'-fluoro-4-[2,3,3',4',6,7-hexahydro-6'-fluorospiro[4H-azepine-4,2'(1'H)naphthalen]-1-(5H)-yl]butyrophenone, hydrochloride (I), 2. 1,2,3,3',4',5,6,7-octahydro-4'-hydroxyspiro[4H-azepine-4,2'-(1'H)naphthalen](VI) with 4-chlorobutyrophenone to obtain 4-[2,3,3',4',6,7-hexahydro-4'-hydroxyspiro[4H-azepine-4,2'(1'H)naphthalen]-1-(5H)-yl]butyrophenone, hydrochloride (I);

3. 1,2,3,3',4',5,6,7-octahydro-4'-exo-methylenespiro[4H-azepine-4,2'(1'H)naphthalene] (VI) with 1-chloro-2-(diethylamino)ethane to obtain 1-[2-(diethylamino)ethyl]-4'-exo-methylenespiro[4H-azepine-4,2'(1'H)naphthalene], dihydrochloride (I);

4. 1,2,3,3',4',5,6,7-octahydro-2-ethylspiro[4H-azepine-4,2'(1'H)naphthalene] (VI) with 3-chloro-N,N-dimethylpropylamine to obtain 1-[3-(dimethylamino)-propyl]-1,2,3,3',4',5,6,7-octahydro-3-ethylspiro[4H-azepine-4,2',(1'H)naphthalene], dihydrochloride (I), and the like.

Other acid addition salts are prepared by substituting the appropriate acid in place of hydrochloric acid.

The free base of the compounds of formula I are prepared by subjecting the acid addition salt to a base such as potassium carbonate as described in Examples 5, 6 and 11, above.

I claim:

1. 4'-fluoro-4-[2,3,6,7-tetrahydrospiro[4H-azepine-4,2'-indan]-1(5H)-yl]butyrophenone, hydrochloride.

2. 4'-fluoro-4[2,3,3',4',6,7-hexahydrospiro[4H-azepine-4,2'-(1'H)naphthalene]-1-(5H)-yl]butyrophenone, hydrochloride.

* * * * *